US010580129B2

(12) United States Patent
Lin et al.

(10) Patent No.: US 10,580,129 B2
(45) Date of Patent: Mar. 3, 2020

(54) HYBRID SPECTROSCOPY IMAGING SYSTEM FOR INTRAOPERATIVE EPILEPTIC CORTEX DETECTION

(71) Applicants: Wei-Chiang Lin, Miami, FL (US); Yinchen Song, Lebanon, NH (US)

(72) Inventors: Wei-Chiang Lin, Miami, FL (US); Yinchen Song, Lebanon, NH (US)

(73) Assignee: The Florida International University Board of Trustees, Miami, FL (US)

( * ) Notice: Subject to any disclaimer, the term of this patent is extended or adjusted under 35 U.S.C. 154(b) by 779 days.

(21) Appl. No.: 15/166,966

(22) Filed: May 27, 2016

(65) Prior Publication Data
US 2017/0340212 A1    Nov. 30, 2017

(51) Int. Cl.
| A61B 5/00 | (2006.01) |
| G06T 7/00 | (2017.01) |
| A61B 5/1455 | (2006.01) |
| A61B 5/055 | (2006.01) |
| G16H 30/20 | (2018.01) |

(Continued)

(52) U.S. Cl.
CPC .......... *G06T 7/0012* (2013.01); *A61B 5/0042* (2013.01); *A61B 5/055* (2013.01); *A61B 5/14551* (2013.01); *A61B 5/14553* (2013.01); *A61B 5/725* (2013.01); *A61B 5/7264* (2013.01); *A61B 5/7275* (2013.01); *A61B 5/7282* (2013.01); *G16H 20/40* (2018.01); *G16H 30/20* (2018.01); *G16H 30/40* (2018.01); *G16H 50/20* (2018.01); *G06K 9/2018* (2013.01);
(Continued)

(58) Field of Classification Search
CPC ........ G06T 7/0012; G06T 2207/30016; A61B 5/7282; A61B 5/725; A61B 5/7264; A61B 5/14553; A61B 5/0042; A61B 5/7275; A61B 5/14551; A61B 5/055; G16H 50/30; G06K 2209/051; G06K 9/2018
See application file for complete search history.

(56) References Cited

U.S. PATENT DOCUMENTS

| 2013/0096408 A1* | 4/2013 | He | A61B 5/04008 600/378 |
| 2014/0276187 A1* | 9/2014 | Iasemidis | A61B 5/4076 600/544 |

OTHER PUBLICATIONS

Spreafico R, et al. (2010) "Focal cortical dysplasias: clinical implication of neuropathological classification systems," Acta Neuropathologica 120(3):359-367.

(Continued)

*Primary Examiner* — Joel Lamprecht
(74) *Attorney, Agent, or Firm* — Saliwanchik, Lloyd & Eisenschenk

(57) ABSTRACT

Methods and systems that detect and differentiate epileptogenic from eloquent and normal cortices are provided. A method for identifying epileptogenic cortices in a brain may include detecting areas in the brain that are undergoing cerebral blood volume low frequency oscillations, detecting areas in the brain that are undergoing blood oxygenation low frequency oscillations; mapping clusters of the brain in which the cerebral blood volume low frequency oscillations are negatively correlated with the blood oxygenation low frequency oscillations, and analyzing the time based relationship between the clusters of the brain that are undergoing negatively correlated low frequency oscillations to determine cause areas, which are areas of the brain that are causing negatively correlated low frequency oscillations to occur elsewhere.

18 Claims, 25 Drawing Sheets

(51) Int. Cl.
G16H 50/20 (2018.01)
G16H 20/40 (2018.01)
G16H 30/40 (2018.01)
G06K 9/20 (2006.01)

(52) U.S. Cl.
CPC ............... G06K 2209/051 (2013.01); G06T 2207/30016 (2013.01)

(56) References Cited

OTHER PUBLICATIONS

Stamatakis EA, et al. (2010) "Changes in resting neural connectivity during propofol sedation," PLoS One 5(12):e14224.
Subasi A, et al. (2010) "EEG signal classification using PCA, ICA, LDA and support vector machines," Expert Systems with Applications 37(12):8659-8666.
Tharin S, et al. (2007) "Functional brain mapping and its applications to neurosurgery," Neurosurgery 60(4):185-202.
Toronov V, et al. (2000) "Near-infrared study of fluctuations in cerebral hemodynamics during rest and motor stimulation: temporal analysis and spatial mapping," Medical Physics 27(4):801-815.
Wang X, et al. (2012) "Effects of propofol and ketamine as combined anesthesia for electroconvulsive therapy in patients with depressive disorder," The Journal of ECT 28(2):128-132.
White BR, et al. (2012) "Bedside optical imaging of occipital resting-state functional connectivity in neonates," NeuroImage 59(3):2529-2538.
Winston GP (2013) "Epilepsy surgery, vision, and driving: What has surgery taught us and could modern imaging reduce the risk of visual deficits?" Epilepsia 54(11):1877-1888.
Yalcin S, et al. (2012) "Ketofol in electroconvulsive therapy anesthesia: two stones for one bird," Journal of Anesthesia 26(4):562-567.
Yang Y, et al (2004) "Simultaneous MRI acquisition of blood volume, blood flow, and blood oxygenation information during brain activation," Magnetic Resonance in Medicine 52(6):1407-1417.
Zavar M, et al. (2011) "Evolutionary model selection in a wavelet-based support vector machine for automated seizure detection," Expert Systems with Applications 38(9):10751-10758.
Zijlmans M, et al. (2012) "Epileptic high-frequency oscillations in intraoperative electrocorticography: The effect of propofol," Epilepsia 53(10):1799-1809.
Alarcon, G., et al. (1997) "Origin and propagation of interictal discharges in the acute electrocorticogram," Brain 120:2259-2282.
Boveroux P, et al. (2010) "Breakdown of within- and between-network resting state functional magnetic resonance imaging connectivity during propofol-induced loss of consciousness," Anesthesiology 113(5):1038-1053.
Buxton RB, et al. (2004) "Modeling the hemodynamic response to brain activation," Neuroimage 23:S220-S233.
Buxton RB (2012) "Dynamic models of Bold contrast," Neuroimage 62(2):953-961.
Cannestra AF, et al. (2000) "Temporal and topographical characterization of language cortices using intraoperative optical intrinsic signals," Neuroimage 12(1):41-54.
Cannestra AF, et al. (2001) "Temporal spatial differences observed by functional MRI and human intraoperative optical imaging," Cerebral Cortex 11(8):773-782.
Chaplot S, et al. (2006) "Classification of magnetic resonance brain images using wavelets as input to support vector machine and neural network," Biomedical Signal Processing and Control 1(1):86-92.
Chen BR, et al. (2014) "A critical role for the vascular endothelium in functional neurovascular coupling in the brain. Journal of the American Heart Association," 3(3):e000787.
Cheng MA, et al. (1996) "Large-dose propofol alone in adult epileptic patients: electrocorticographic results," Anesthesia & Analgesia 83(1):169-174.

Choi H, et al. (2014) "Abnormal metabolic connectivity in the pilocarpine-induced epilepsy rat model: a multiscale network analysis based on persistent homology," NeuroImage 99:226-236.
Cui Z & Luan G (2011) "A venous malformation accompanying focal cortical dysplasia resulting in a reorganization of language-eloquent areas," Journal of Clinical Neuroscience 18(3):404-406.
Dachet F, et al. (2014) "Predicting novel histopathological microlesions in human epileptic brain through transcriptional clustering," Brain:awu350.
Ding Z, et al. (2002) "Anesthesia for electroconvulsive therapy," Anesthesia & Analgesia 94(5):1351-1364.
El-Naqa I, et al (2002) "A support vector machine approach for detection of microcalcifications," Medical Imaging, IEEE Transactions on 21(12):1552-1563.
Fox MD, et al. (2007) "Spontaneous fluctuations in brain activity observed with functional magnetic resonance imaging," Nature Reviews Neuroscience 8(9):700-711.
Gasser T, et al. (2005) "Intraoperative functional MRI: implementation and preliminary experience," Neuroimage 26(3):685-693.
Glover GH (1999) "Deconvolution of Impulse Response in Event-Related Bold fMRI1," Neuroimage 9(4):416-429.
Guo L, et al. (2010) "Automatic epileptic seizure detection in EEGs based on line length feature and artificial neural networks," Journal of neuroscience methods 191(1):101-109.
Haglund MM, et al. (2004) "Optical imaging of epileptiform activity in human neocortex," Epilepsia 45(s4):43-47.
Hamilton NB, et al. (2010) "Pericyte-mediated regulation of capillary diameter: a component of neurovascular coupling in health and disease," Frontiers in Neuroenergetics 2.
Hufnagel A, et al.(1990) "Specific response of the epileptic focus to anesthesia with propofol," Journal of Epilepsy 3(1):37-45.
Jayakar P, et al. (1994) "Subdural monitoring in the evaluation of children for epilepsy surgery," Journal of child neurology 9(2 suppl):2S61-62S66.
Jayakar P, et al. (2008) "Epilepsy surgery in patients with normal or nonfocal MRI scans: integrative strategies offer long-term seizure relief," Epilepsia 49(5):758-764.
Jupp B, et al. (2012) "Hypometabolism precedes limbic atrophy and spontaneous recurrent seizures in a rat model of TLE," Epilepsia 53(7):1233-1244.
Kalkman C, et al. (1991) "Differential effects of propofol and nitrous oxide on posterior tibial nerve somatosensory cortical evoked potentials during alfentanil anaesthesia," British Journal of Anaesthesia 66(4):483-489.
Krieger SN, et al. (2014) "Simultaneous acquisition of cerebral blood volume-, blood flow-, and blood oxygenation-weighted MRI signals at ultra-high magnetic field," Magnetic Resonance in Medicine.
Krsek P, et al. (2013) "Predictors of seizure ©\free outcome after epilepsy surgery for pediatric tuberous sclerosis complex," Epilepsia 54(11):1913-1921.
Lavine M, et al. (2011) "Dynamic linear model analysis of optical imaging data acquired from the human neocortex," Journal of Neuroscience Methods 1992:346-362.
Liwnicz BH, et al. (1990) "Pericyte degeneration and thickening of basement membranes of cerebral microvessels in complex partial seizures: electron microscopic study of surgically removed tissue," Neurosurgery 26(3):409-420.
Lu H, et al. (2003) "Functional magnetic resonance imaging based on changes in vascular space occupancy," Magnetic Resonance in Medicine 50(2):263-274.
Luo Q, et al. (2013) "Spatio-temporal Granger causality: a new framework," NeuroImage 79:241-263.
Mallat SG (1989) "A theory for multiresolution signal decomposition: the wavelet representation," Pattern Analysis and Machine Intelligence, IEEE Transactions on 11(7):674-693.
Mayhew JE, et al. (1996) "Cerebral vasomotion: a 0.1-Hz oscillation in reflected light imaging of neural activity," Neuroimage 4(3):183-193.
McCaslin AF, et al. (2011) "In vivo 3D morphology of astrocyte-vasculature interactions in the somatosensory cortex: implications for neurovascular coupling," Journal of Cerebral Blood Flow & Metabolism 31(3):795-806.

(56) References Cited

OTHER PUBLICATIONS

Mhuircheartaigh RN, et al. (2010) "Cortical and subcortical connectivity changes during decreasing levels of consciousness in humans: a functional magnetic resonance imaging study using propofol," The Journal of Neuroscience 30(27):9095-9102.

Nasiriavanaki M, et al. (2014) "High-resolution photoacoustic tomography of resting-state functional connectivity in the mouse brain," Proceedings of the National Academy of Sciences 111(1):21-26.

Ndode-Ekane X, et al. (2010) "Vascular changes in epilepsy: functional consequences and association with network plasticity in pilocarpine-induced experimental epilepsy," Neuroscience 166(1):312-332.

Paolicchi J, et al. (2000) "Predictors of outcome in pediatric epilepsy surgery," Neurology 54(3):642-642.

Pondal-Sordo M, et al. (2007) "Usefulness of intracranial EEG in the decision process for epilepsy surgery," Epilepsy research 74(2):176-182.

Ramirez J, et al. (2013) "Computer-aided diagnosis of Alzheimer's type dementia combining support vector machines and discriminant set of features," Information Sciences 237:59-72.

Rayshubskiy A, et al. (2014) "Direct, intraoperative observation of~ 0.1 Hz hemodynamic oscillations in awake human cortex: implications for fMRI," Neuroimage 87:323-331.

Rigau V, et al. (2007) "Angiogenesis is associated with blood-brain barrier permeability in temporal lobe epilepsy," Brain 130(7):1942-1956.

Roebroeck A, et al (2005) "Mapping directed influence over the brain using Granger causality and fMRI," NeuroImage 25(1):230-242.

Sato K, et al. (2002) "Intraoperative intrinsic optical imaging of neuronal activity from subdivisions of the human primary somatosensory cortex," Cerebral Cortex 12(3):269-280.

Scanley BE, et al. (1997) "Functional magnetic resonance imaging of median nerve stimulation in rats at 2.0 T," Magnetic Resonance in Medicine 37(6):969-972.

Sliwka U, et al. (2001) "Spontaneous oscillations in cerebral blood flow velocity give evidence of different autonomic dysfunctions in various types of headache," Headache: The Journal of Head and Face Pain 41(2):157-163.

Sobottka SB, et al. (2013) "Intraoperative optical imaging of intrinsic signals: a reliable method for visualizing stimulated functional brain areas during surgery: Clinical article," Journal of Neurosurgery 119(4):853-863.

Sommer B, et al. (2013) "Integration of functional neuronavigation and intraoperative MRI in surgery for drug-resistant extratemporal epilepsy close to eloquent brain areas," Neurosurgical Focus 34(4):E4.

Song Y, et al. (2012) "Low-frequency pathophysiological characteristics of pediatric epileptic cortex during the interictal period detected using a dual-wavelength imaging system," SPIE Medical Imaging, (International Society for Optics and Photonics), pp. 83170V-83170V-83178.

Song Y, et al (2015) "Distributions of irritative zones are related to individual alterations of resting-state networks in focal epilepsy," PLos One 10(7): e0134352.

\* cited by examiner

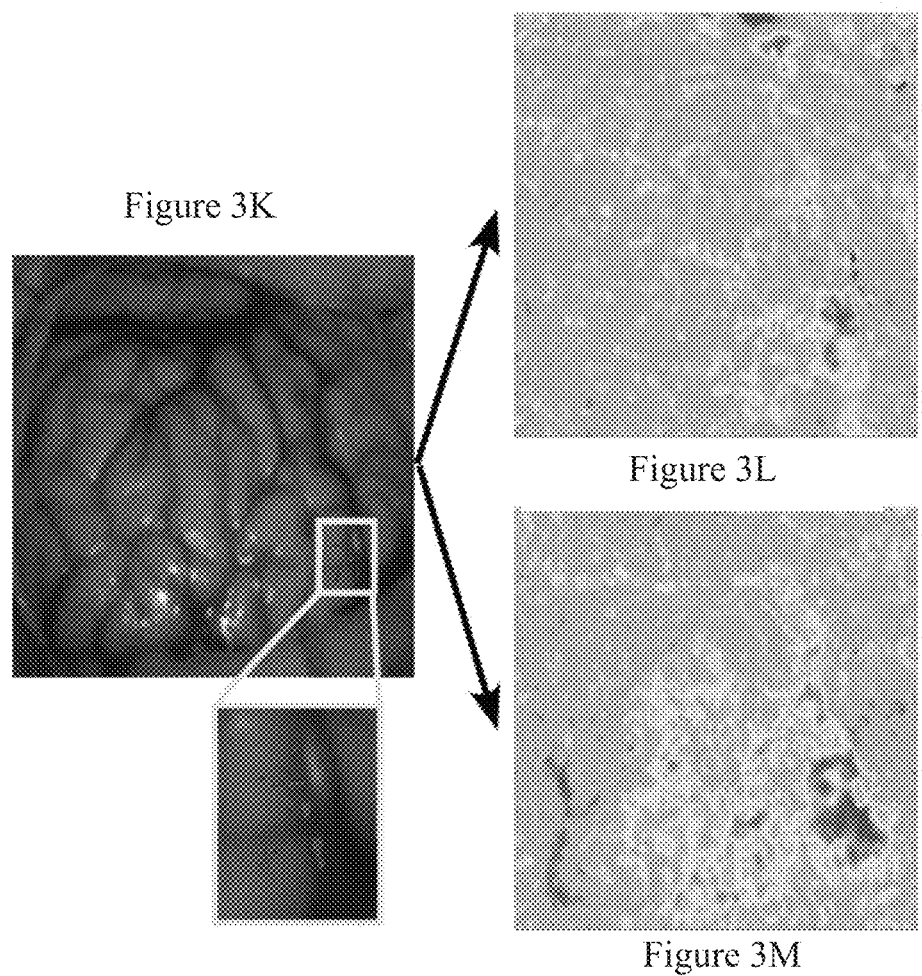

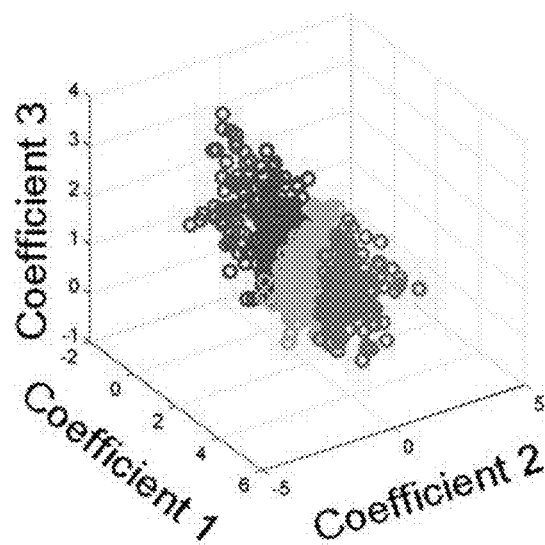
Figure 4E
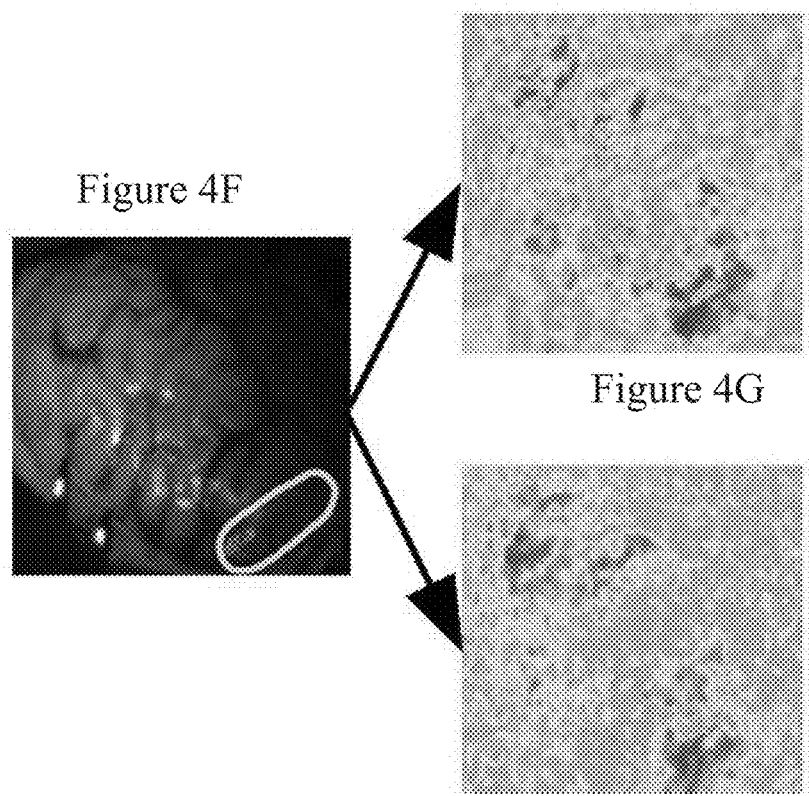
Figure 4F
Figure 4G
Figure 4H

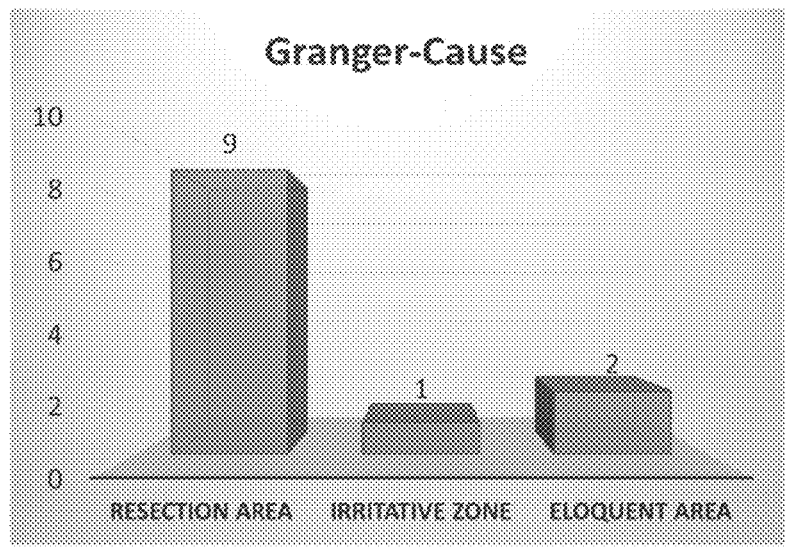
Figure 5A
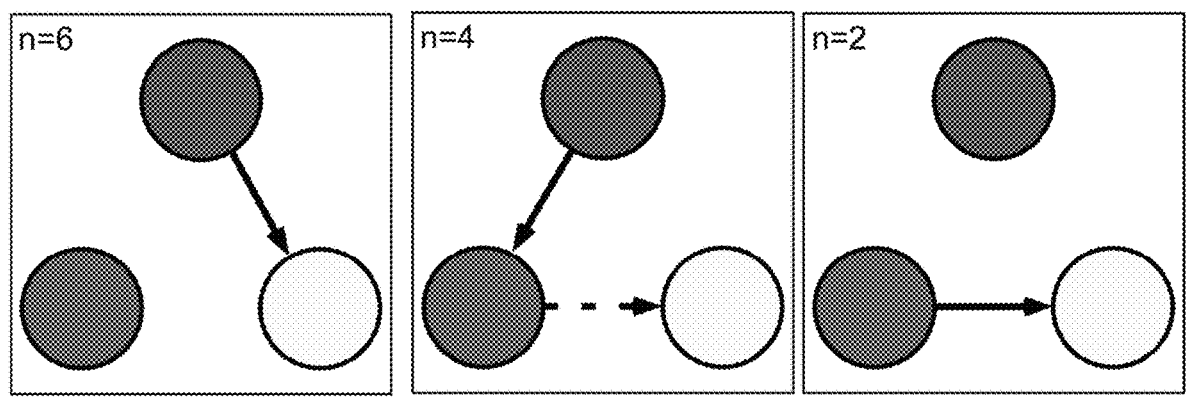
(single-column)
Figure 5B     Figure 5C     Figure 5D
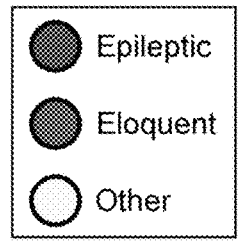

(single-column)

HYBRID SPECTROSCOPY IMAGING SYSTEM FOR INTRAOPERATIVE EPILEPTIC CORTEX DETECTION

BACKGROUND

Removal of epileptogenic brain areas in which seizures originate offers patients with refractory epilepsy the chance of being seizure free. However, this resection must be balanced against the preservation of eloquent cortical areas to reduce postoperative morbidity. Many screening technologies based on the occurrence of both inter-ictal and ictal abnormal activities have been used during the preoperative evaluation phase for epilepsy surgeries, including electroencephalograms (EEG), functional magnetic resonance imaging (fMRI), positron emission tomography (PET), and single-photon emission computed tomography (SPECT). Together, they provide the general location but not the exact boundaries of seizure-inducing brain areas. In addition, the usefulness of information provided by these non-invasive techniques degrades during the course of surgery because of brain shifting and deformation that is invariably induced by the loss of cerebrospinal fluid.

Electrocorticography (ECoG) has been demonstrated to be a valuable intraoperative tool, not only to precisely delineate such boundaries, but also to identify eloquent cortical areas. However, the technique requires prolonged recordings with electrodes implanted long-term, thereby elevating the risks of hemorrhage, infection and cerebral edema. Intraoperative MRI (iMRI) and fMRI (ifMRI) have recently started to play crucial roles in epilepsy surgery, as they enable the maximum extent of resection despite the lesion's proximity to eloquent brain cortex and fiber tracts which, in turn, leads to favorable seizure-reduction outcomes and acceptable neurological deficit rates. Unfortunately, the use of iMRI or ifMRI demands an extremely high standard of infrastructure and maintenance. As a result, only a limited number of hospitals and research institutes have the financial and technical capabilities to offer these technologies for routine patient care. In addition, the functional mapping of ifMRI relies on the selection of hemodynamic response functions, which could compromise the accuracy of localization.

BRIEF SUMMARY

Due to the problems discussed above, additional preoperative and intraoperative evaluations are needed for finalizing surgical plans and guiding surgery during epileptogenic resection. Embodiments of the present invention include methods and systems that detect and differentiate epileptogenic from eloquent and normal cortices. Embodiments of the present invention can provide intraoperative epileptogenic cortex detection, and hence improve the outcome of epilepsy surgery. Embodiments of the present invention may also be incorporated in combination with other methods of detecting epileptic cortices, for example, electrocorticography (ECoG), in determining a surgical plan and in guiding surgery. The present invention may be particularly useful with patients having focal epilepsy.

In an embodiment of the present invention, a method for identifying epileptogenic cortices in a brain can include: detecting areas in the brain that are undergoing cerebral blood volume low frequency oscillations; detecting areas in the brain that are undergoing blood oxygenation low frequency oscillations; mapping clusters of the brain in which the cerebral blood volume low frequency oscillations are negatively correlated with the blood oxygenation low frequency oscillations; and analyzing the time based relationship between the clusters of the brain that are undergoing negatively correlated low frequency oscillations to determine cause areas, which are areas of the brain that are causing negatively correlated low frequency oscillations to occur elsewhere. The method may further include identifying the cause areas as potential epileptogenic cortex and using the identified cause areas for surgical planning or guiding epileptogenic resection intraoperatively. The low frequency oscillations can be in a range of from about 0.01 Hz to about 0.2 Hz or, more narrowly, in a range of from about 0.02 Hz to about 0.1 Hz.

According to some embodiments, the detecting of areas in the brain that are undergoing cerebral blood volume low frequency oscillations and the detecting of areas in the brain that are undergoing blood oxygenation low frequency oscillations is accomplished by capturing images of a surface of the brain within a wavelength range of 300 nm to 800 nm. The detecting of areas in the brain that are undergoing cerebral blood volume low frequency oscillations may be accomplished by analyzing images within a wavelength range of about 400 nm to about 595 nm, and the detecting of areas in the brain that are undergoing blood oxygenation low frequency oscillations may be accomplished by analyzing images having a wavelength range of about 640 to 750 nm.

In some embodiments, the detecting of areas in the brain that are undergoing cerebral blood volume low frequency oscillations and the detecting of areas in the brain that are undergoing blood oxygenation low frequency oscillations is accomplished by capturing images of a surface of the brain with a wavelength band that is indicative of cerebral blood volume and capturing images of the surface of the brain with a wavelength band that is indicative of blood oxygenation.

In some embodiments, the capturing of images of the surface of the brain with the wavelength band that is indicative of cerebral blood volume and the capturing of images of the surface of the brain with the wavelength band that is indicative of blood oxygenation includes is accomplished using a dichroic mirror. In addition to a dichroic mirror, or instead of using a dichroic mirror, bandpass filters may be used to separate wavelengths indicative of cerebral blood volume from wavelengths indicative of blood oxygenation. In some embodiments, hardware, software, or a combination of hardware and software is used to separate a wavelength band that is indicative of hemoglobin oxygenation from a wavelength band that is indicative of cerebral blood volume. The methods can further include image preprocessing, such as co-registering, cropping, and smoothing the images, before the images are analyzed to determine areas that are exhibiting low frequency oscillations.

In some embodiments, the detecting of areas in the brain that are undergoing cerebral blood volume low frequency oscillations and the detecting of areas in the brain that are undergoing blood oxygenation low frequency oscillations can be accomplished using a non-invasive imaging modality. The non-invasive imaging modality may include functional magnetic resonance imaging (fMRI).

In an embodiment of the present invention, a system for identifying epileptogenic cortices in a brain may include: a means for identifying areas in the brain that are exhibiting cerebral blood volume low frequency oscillations; a means for identifying areas in the brain that are exhibiting blood oxygenation low frequency oscillations; a means for identifying clusters of the brain that are exhibiting a negative correlation (negatively correlated areas) between the cerebral blood volume low frequency oscillations and the blood oxygenation low frequency oscillations; and a means for identifying one or more cause areas, wherein the cause areas are negatively correlated areas that propagate or cause negatively correlated low frequency oscillations in other areas of the brain. In some embodiments, the means for identifying areas in the brain that are exhibiting cerebral blood volume low frequency oscillations and the means for identifying areas in the brain that are exhibiting blood oxygenation low frequency oscillations include a non-invasive imaging modality. The non-invasive imaging modalities can include fMRI.

In some embodiments, the means for identifying areas in the brain that are exhibiting cerebral blood volume low frequency oscillations and the means for identifying areas in the brain that are exhibiting blood oxygenation low frequency oscillations include: one or more image recording devices suitable for capturing images of a surface of the brain over time; one or more processors suitable for separating the images into a wavelength band that is indicative of hemoglobin oxygenation and a wavelength band that is indicative of cerebral blood volume concentration; and/or one or more processors suitable for identifying low frequency oscillations within the hemoglobin oxygenation indicative wavelength band and suitable for identifying low frequency oscillations within the cerebral blood volume indicative wavelength band.

In some embodiments, the means for identifying clusters in the brain that are exhibiting cerebral blood volume low frequency oscillations and blood oxygenation low frequency oscillations includes: a dichroic mirror suitable for separating a wavelength band that is indicative of hemoglobin oxygenation and a wavelength band that is indicative of cerebral blood volume concentration; a first image recording device positioned to capture wavelengths transmitted through a dichroic mirror; and/or a second image recording device positioned to capture wavelengths that are reflected by the dichroic mirror. The dichroic mirror can have a transmission wavelength range of about 400 nm to 595 nm and a reflection wavelength range of about 640 nm to 750 nm. In place of or in combination with a dichroic mirror, some embodiments include a first bandpass filter that is approximately a 500 nm bandpass filter and a second bandpass filter that is approximately a 700 nm bandpass filter, wherein each of the first bandpass filter and the second bandpass filter is positioned between the dichroic mirror and its respective image recording devices.

BRIEF DESCRIPTION OF THE DRAWINGS

FIG. 3K is an image showing the identification of Granger-causes.

FIG. 3L is an image of a correlation coefficient map (CCM) for Granger-causes at 500 nm.

FIG. 3M is an image of a correlation coefficient map (CCM) for Granger-causes at 700 nm.

FIG. 4E is a 3-D scatter plot of clustering features.

FIG. 4F is an image showing the identification of Granger-causes with the resection area outlined.

FIG. 4G is an image of a correlation coefficient map (CCM) for Granger-causes at 500 nm.

FIG. 4H is an image of a correlation coefficient map (CCM) for Granger-causes at 700 nm.

FIG. 5A is a graph illustrating the number of patients having Granger-causes in a particular area.

FIGS. 5B through 5D illustrate the number of patients each having a particular causality sequence.

FIG. 7A illustrates an autoregressive model with an exogenous source (ARX).

FIG. 7B illustrates corresponding impulse response functions (IRFs) obtained from epileptogenic and eloquent areas.

FIG. 7C illustrates that the hyper-plane obtained by the support vector machine (SVM) was able to separate epileptogenic cortex from eloquent areas with a sensitivity of 93% and a specificity of 70% (n=25, 15 epileptogenic and 10 eloquent areas).

DETAILED DESCRIPTION

Complete removal of epileptogenic cortex while preserving eloquent areas is crucial in patients undergoing epilepsy surgery. Embodiments of the present invention include methods and systems that detect and differentiate epileptogenic from eloquent and normal cortices. Embodiments of the present invention can provide intraoperative epileptogenic cortex detection, and hence improve the outcome of epilepsy surgery. Embodiments of the present invention may also be incorporated in combination with other methods of detecting epileptic cortices, for example, electrocorticography (ECoG), in determining a surgical plan and in guiding surgery.

Embodiments of the present invention include methods and systems that record images of the brain over a period of time. Using the time based recordings, areas of the brain that exhibit low-frequency oscillations (LFOs) in cerebral blood volume (CBV) and hemoglobin oxygenation (oxygenation) are identified. The LFOs may be in the range from about 0.01 Hz to about 0.2 Hz or, more narrowly, in a range of from about 0.02 Hz to about 0.1 Hz. After areas of the brain exhibiting LFOs are detected, further analysis can be conducted to determine which areas of the brain experiencing LFOs are demonstrating negative correlations between cerebral blood volume and blood oxygenation (negatively correlated LFOs). In other words, embodiments of the present invention can determine which areas of the brain are experiencing cerebral blood volume LFOs and oxygenation LFOs that are in phase and out of phase, and those that are out of phase are defined as "negatively correlated LFOs."

Figure 11:
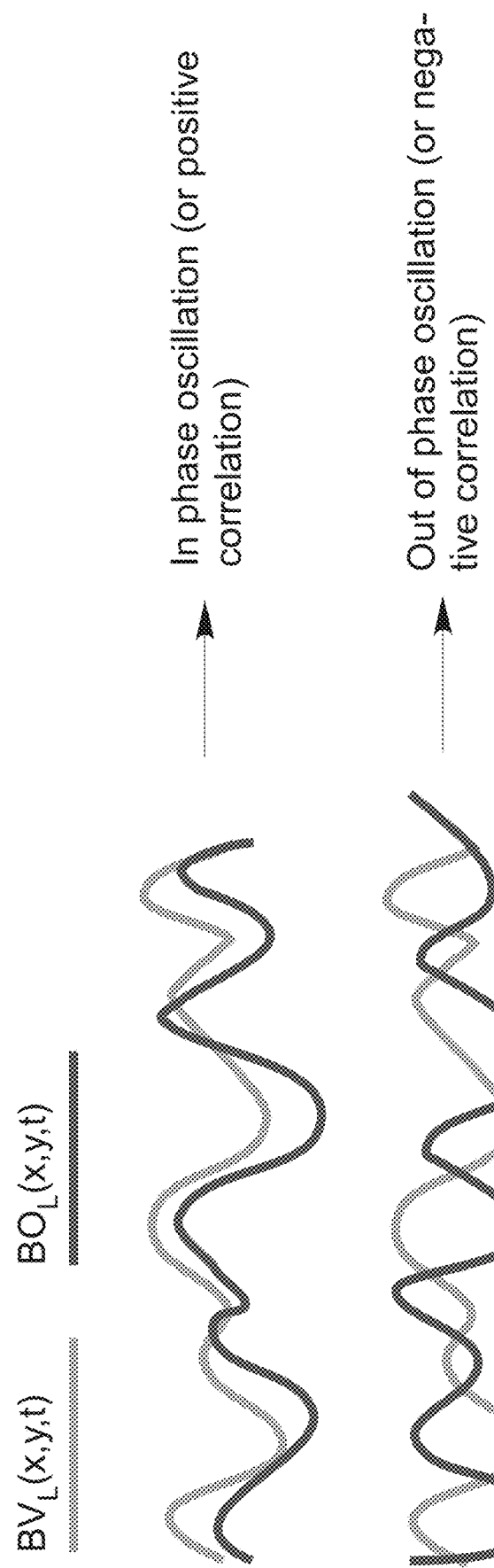
FIG. 11 is an illustration demonstrating in-phase and out-of-phase low frequency oscillations (LFOs) of cerebral blood volume $BV_L(x,y,t)$ and blood oxygenation $BO_L(x,y,t)$.

FIG. 11 is an illustration demonstrating an example of in-phase and out-of-phase low frequency oscillations (LFOs) of cerebral blood volume BVL(x,y,t) and blood oxygenation BOL(x,y,t).

After the areas of the brain that are demonstrating negatively correlated LFOs (i.e., a negative correlation between blood oxygenation and cerebral blood volume) are mapped, embodiments of the present invention may further analyze the time based relationship between the negatively correlated LFOs. Specifically, it can be determined which areas of the brain experiencing negatively correlated LFOs are causing negatively correlated oscillations in other areas of the brain. The areas that are determined to be the source or sources of negatively correlated LFO propagation ("cause areas") may be determined to be epileptogenic cortex and may help in surgical planning and guiding epileptogenic resection intraoperatively.

In some embodiments of the present invention, CBV and oxygenation can be determined using electromagnetic radiation that is near or within the visible spectrum. That is, light reflecting off the cortical surface of the brain can be measured and analyzed to determine CBV and oxygenation as a function of time. The recordings may be captured using a dynamic intrinsic optical signal imaging (DIOSI) system. The light may be separated into two different wavelength bands before being analyzed. Specifically, the light may be separated into one wavelength band that is indicative of CBV and another wavelength band that is indicative of oxygenation. The wavelength band indicative of CBV may be approximately 500 nm, and the wavelength band indicative of oxygenation may be approximately 700 nm.

Figure 10A:
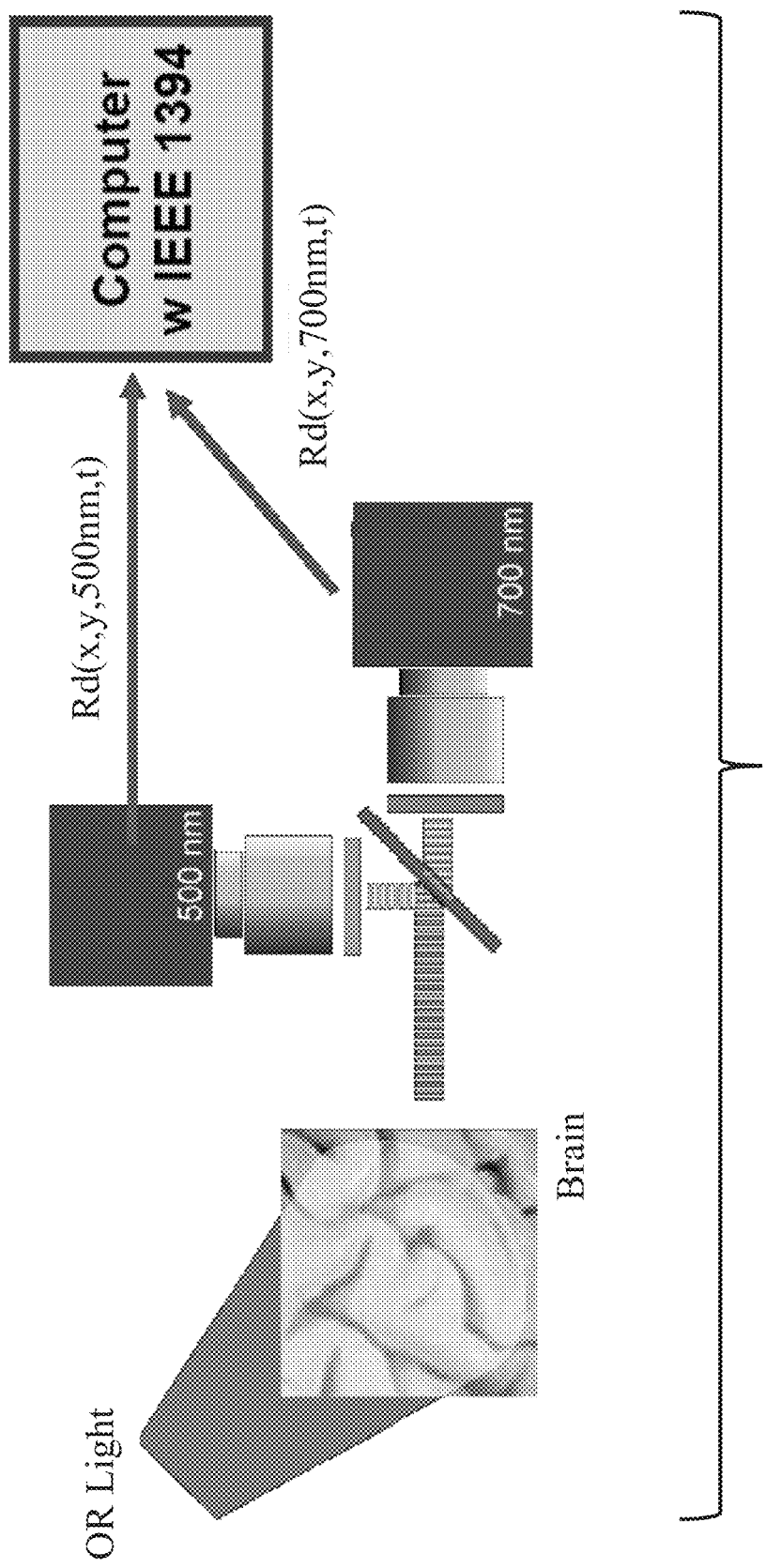
FIG. 10A is a schematic diagram of a dynamic intrinsic optical signal imaging (DIOSI) system according to an embodiment of the present invention.
Figure 10B:
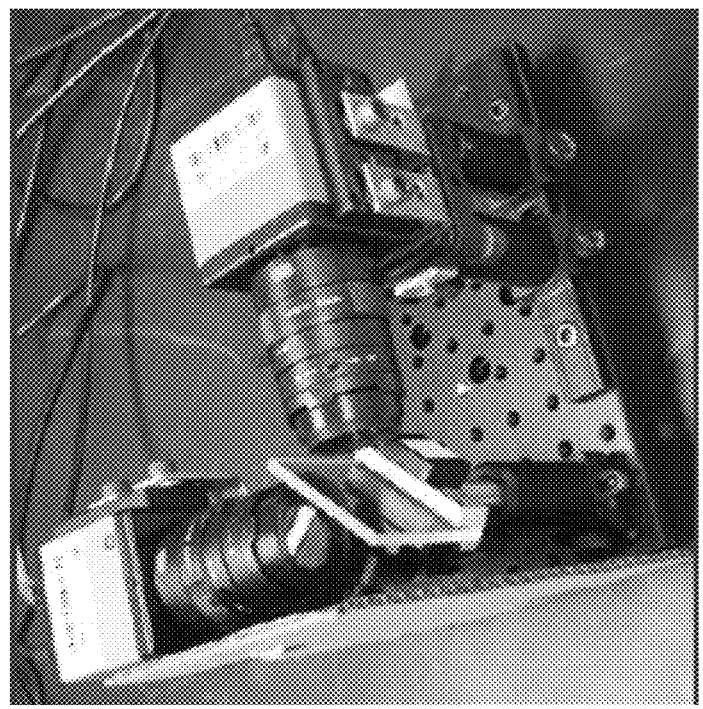
FIG. 10B is an image of a dynamic intrinsic optical signal imaging (DIOSI) system according to an embodiment of the present invention.

The light reflecting off the cortical surface of the brain may initially be separated into two wavelength bands using a dichroic mirror. The dichroic mirror may have a transmission wavelength range from about 400 nm to about 595 nm, and a reflection wavelength range from about 640 nm to about 750 nm. Two or more digital image recording devices (i.e., digital cameras or video recorders) may be provided, one for recording the wavelength band indicative of CBV and one for recording the wavelength band indicative of oxygenation. FIG. 10A is a schematic diagram of a dynamic intrinsic optical signal imaging (DIOSI) system according to an embodiment of the present invention. FIG. 10B is an image of a dynamic intrinsic optical signal imaging (DIOSI) system according to an embodiment of the present invention.

The two or more digital cameras can be synchronized and capture images continuously at a frequency and period of time suitable for detecting LFOs. For example, the images may be captured at a frequency range from about 2 Hz to about 10 Hz for a period of time from approximately two minutes to approximately ten minutes. Before the light is transmitted to and recorded by the digital image recording devices, each of the wavelength bands transmitted through and reflected by the dichroic mirror may pass through one or more additional bandpass filters. For example, the light transmitted through the dichroic mirror may pass through a 500 nm band-pass filter and the light reflected off of the dichroic mirror may pass through a 700 nm bandpass filter. Instead of using bandpass filters and/or dichroic mirrors to filter light into CBV and oxygenation wavelength bands, this process may instead be accomplished by computer hardware, software, or a combination of both hardware and software.

After capturing the images using the digital image recording device(s), each of the 500 nm (or CBV indicative) images and 700 nm (or oxygenation indicative) images may be co-registered and cropped to show the same exposed cortex areas, and both the 500 nm images and the 700 nm images may be smoothed using a spatial averaging filter. A time series may be analyzed for each pixel R(x,y,t) in both a time domain and a frequency domain. The time series R(p,t) may be filtered, where p=(x,y), using a band-pass FIR filter (~0.02-0.1 Hz) to give Rlow (p,t). Artifacts (originating from light source and vessel movements) may be removed from Rlow (p,t) using a principal component analysis method to give Rpca (p,t) at each pixel. A power spectral density map may be generated using Rpca (p,t) for each of the 500 nm and 700 nm wavelengths. A correlation coefficient map (CCM) may then be created by calculating the extent of correlation between Rpca (p,t) at 500 nm and 700 nm for each pixel. Pixels with negative correlations may then be extracted from the CCM and isolated pixels can be removed to leave only spatially connected pixel groups (using an arbitrary threshold of, for example, 25 pixels to identify those spatially-connected pixel groups). The pixels may then be classified into multiple clusters, using a mean shift clustering method, based upon their temporal profiles in Rpca (p,t) at both the 500 nm and 700 nm wavelengths. The Rpca (p,t) of each of the clusters may be denoted as Rci (p,t), wherein the subscript i stands for the cluster number.

After the clusters Rci (p,t) have been identified, the effective and functional connectivity of the clusters as Rci (p,t) may then be analyzed, wherein the analyzing the effective and functional connectivity of the clusters can be as follows. A Granger causality analysis may be applied for non-stationary signals to mean values of Rci (p,t) at 500 nm (Rcibar (p,t). Influences that originate in A regions and are imposed on B regions may then be determined (called "directed influences"). The A regions can then be labeled Granger-causes and the B regions can be labeled Granger-effects when Rcibar (p,t) of the A regions are determined to have a directed influence on the Rcibar (p,t) of the B regions. The Granger-causes and Granger-effects may then be used as a reference to calculate seed-based correlation coefficients with Rpca (p,t) from other pixels within the field of view (FOV) at both the 500 nm and 700 nm wavelengths, to thereby demonstrate functional brain connectivity.

Figure 1A:
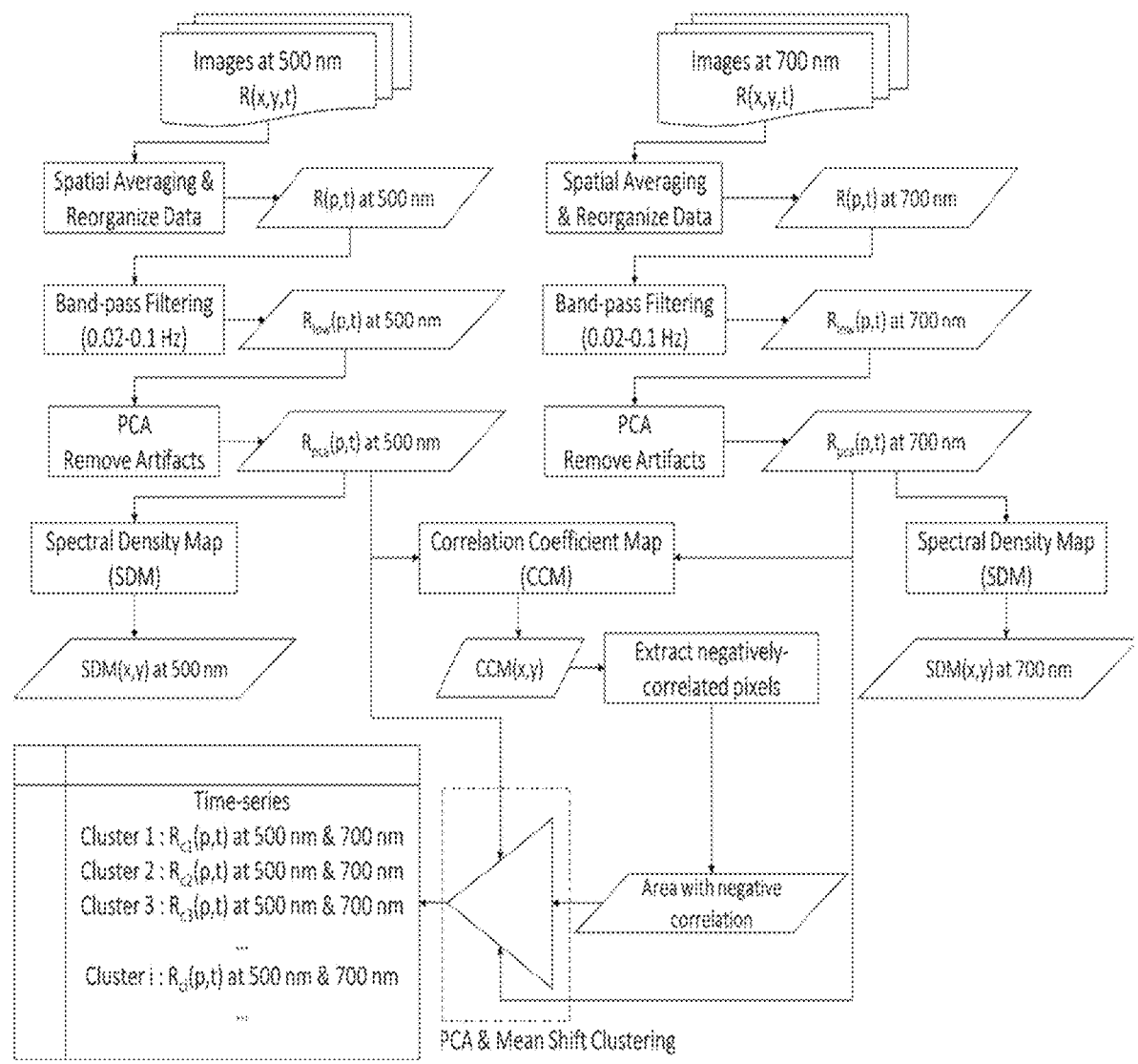
FIG. 1A is a flow chart illustrating the preprocessing of optical image data according to an embodiment of the present invention.
Figure 1B:
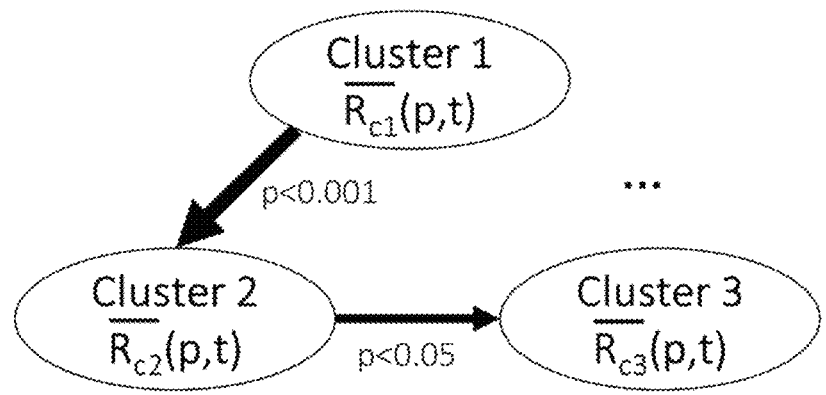
FIG. 1B illustrates the investigation of effective and functional brain connectivity according to an embodiment of the present invention.
Figure 1B:
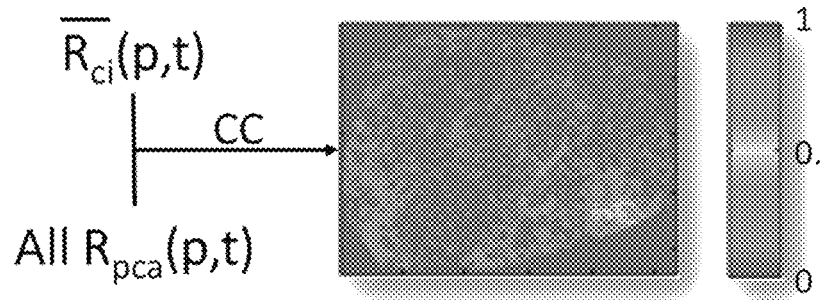
Figure 1C:
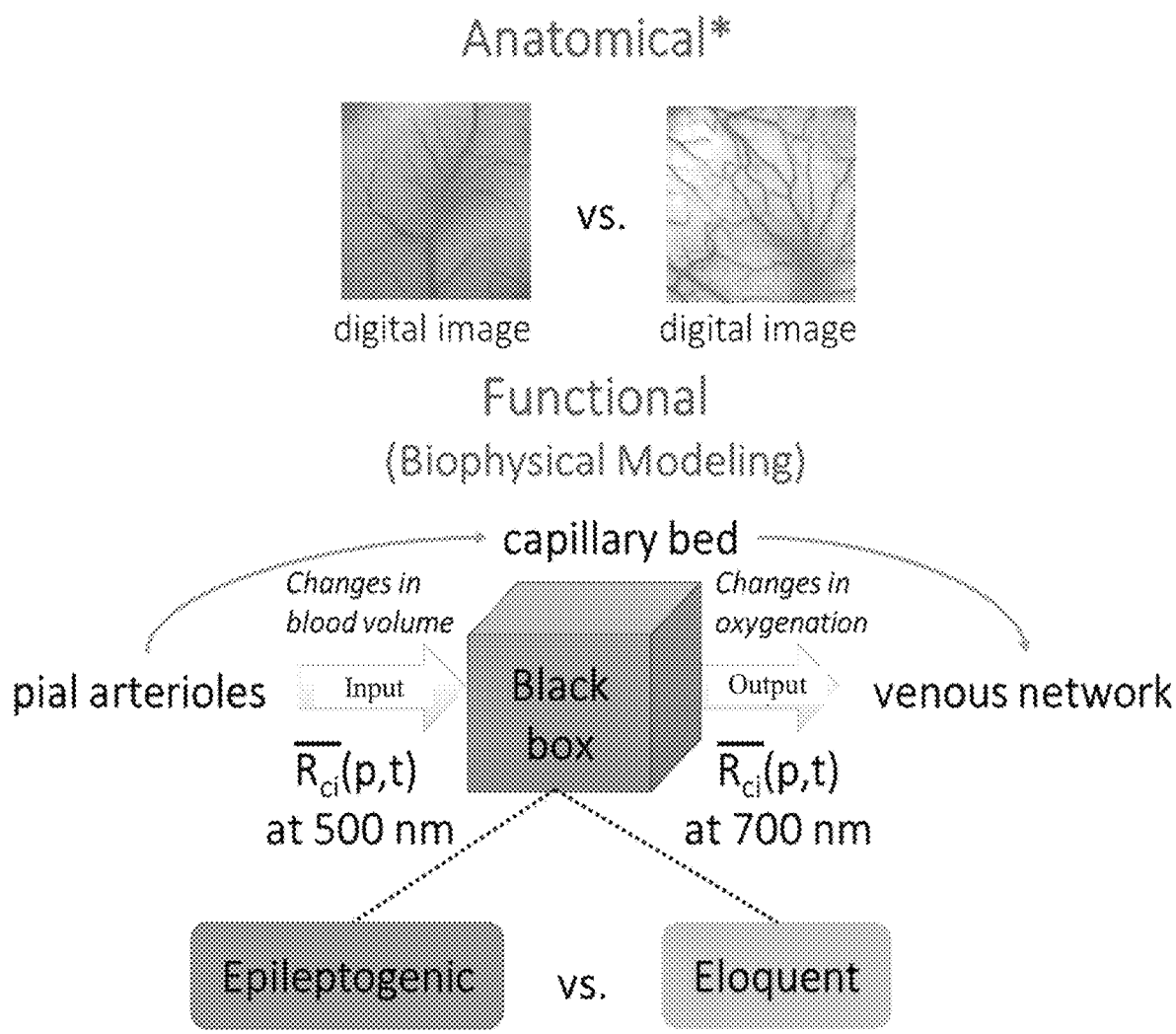
FIG. 1C illustrates the quantitative assessment in vascular networks from both anatomical and functional perspectives, according to an embodiment of the present invention.

FIG. 1A is a flow chart illustrating the preprocessing of optical image data according to an embodiment of the present invention. The main purpose of the preprocessing of image data shown in FIG. 1A is to remove artifacts and identify negatively-correlated hemodynamic low-frequency oscillatory signals (LFOs). As seen in FIG. 1A, embodiments of the present invention can include spatial averaging and reorganizing data, band-pass filtering, removing artifacts using principal component analysis (PCA), and producing a spectral density map for both 500 nm images and 700 nm images (i.e., images that represent CBV and oxygenation). Next, a correlation coefficient map (CCM) can be created, negatively correlated pixels can be extracted, and areas with negative correlations between CBV and oxygenation can be determined. FIG. 1B illustrates the investigation of effective and functional connectivity brain activity according to an embodiment of the present invention. According to FIG. 1B, Granger causality analysis is used to determine which negatively correlated areas are causing negatively correlated areas to occur elsewhere in the brain. FIG. 1C illustrates the quantitative assessment in vascular networks from both anatomical and functional perspectives, according to an embodiment of the present invention.

As discussed above, the relationship between the LFOs obtained by DIOSI at 500 nm and 700 nm can be used as a biomarker to distinguish epileptogenic from normal/eloquent cortex. Because of its limited penetration depth, at this time it is difficult to use DIOSI to detect deep-seated epileptogenic foci. In addition, the success of DIOSI at mapping epileptogenic cortex intraoperatively may depend on accurate pre-operative localizations based on other neuro-imaging modalities. If the pre-operative imaging fails to provide sufficient information to localize all the epileptogenic cortices, the DIOSI may be limited to detecting only those that are located inside the exposed cortical areas. Unfortunately, despite all the current technologies available for epilepsy surgery, only about 65% of epilepsy surgery patients achieve a good postoperative outcome. Consequently, it would be beneficial to non-invasively detect all epileptogenic areas pre-operatively if intraoperative DIOSI is to delineate them.

Since fluctuations in DIOSI at 500 nm and 700 nm are related to changes in CBV and oxygenation, it is possible to detect these physiological characteristics using non-invasive imaging modalities like fMRI. Functional MRI is capable of measuring blood oxygenation level dependent (BOLD) signals that are associated with regional hemodynamics, as well as metabolic parameters like the oxygen extraction ratio, $CMRO_2$, CBF, and CBV. In addition, fMRI can measure vascular space occupancy (VASO), which provides indirect access to the changes in CBV associated with neuronal activity. Simultaneous BOLD-fMRI and VASO-fMRI have been performed to study functionally-induced BOLD and CBV responses in the human brain. The same technique can be used to acquire BOLD and CBV signals from epileptogenic brain tissue in a non-invasive fashion, with data interpreted using the approaches disclosed in this application, thereby allowing for epileptogenic cortex to be identified and separated from normal/eloquent cortex.

The methods to identify epileptogenic cortex according to embodiments of the subject invention can be conducted on epilepsy patients under anesthesia during surgery. They do not require any external stimulation or any reduction in anesthesia to map eloquent areas. This makes DIOSI a promising, complementary tool for intraoperative guidance. It could also provide more specific direction regarding where to place subdural electrodes for ECoG recordings. One challenge related to certain methods of embodiments of the subject invention is DIOSI's susceptibility to artifacts induced by specular reflection, because human cortical surfaces are not flat. To overcome these artifacts of specular reflection, DIOSI acquisition can be focused on one area of the exposed cortical surface at a time, as well as at different locations and from different viewing angles.

The methods and processes of some of the embodiments described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various readonly-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the present invention and of its many advantages may be had from the following example, given by way of illustration. The following example is illustrative of some of the methods, applications, embodiments and variants of the present invention. It is, of course, not to be considered as limiting the invention. Numerous changes and modifications can be made with respect to the invention.

Example 1

A study was performed to verify the theories and techniques that are applied in embodiments of the present invention. The study was conducted with data acquired from eleven pediatric patients that underwent epilepsy surgery for focal epilepsy. During each DIOSI study, the patient was kept still and his or her physiological condition was kept stable under normal anesthesia.

Images at 500 nm and 700 nm were acquired simultaneously and continuously from the exposed cortical surface intraoperatively using a dynamic intrinsic optical signal imaging (DIOSI) system. The exposed cortex was illuminated by surgical light in the operating room and imaged through a NIKON™ dSLR lens (NIKON™ AF 28-80 mm f/3.5-5.6 D Lens with Aperture Ring). Images were re-collimated and then split into two branches using a dichroic mirror (#49-471, EDMUND OPTICS™) with a transmission wavelength range of 400-595 nm and a reflection wavelength range of 640-750 nm. Two CCD cameras (DMK 21AU04, THE IMAGING SOURCE™ Europe GmbH) were attached to the holder of the dichroic mirror: one at the transmission port ($Cam_T$) and the other at the reflection port ($Cam_R$). The $Cam_T$ recorded images through a 500 nm band-pass filter (#65-149, EDMUND OPTICS™) and the $Cam_R$ through a 700 nm band-pass filter (#88-012, EDMUND OPTICS™). Both cameras were synchronized using external triggers provided by a function generator. In each single-image acquisition sequence, at least 1000 frames were acquired by each camera at a rate of five frames per second. The imaging system was controlled by a LABVIEW™ program via an IEEE 1394a interface.

The procedures described below were part of a protocol provided to epilepsy surgery candidates. For patients undergoing two-stage epilepsy surgery, the ECoG electrode arrays were placed on top of the cortical surface following an optical imaging acquisition procedure. Placement of the ECoG electrode arrays was determined by the results of the pre-operative evaluations using scalp EEG, MRI/fMRI, PET and/or SPECT, which were not influenced by the results of DIOSI data analysis. After the first-stage surgery, the electrical activities of the target cortex of the patients were monitored for at least one week to identify the brain areas producing the ictal/inter-ictal spikes. The final decision on the area of resection was determined by the ECoG results, in conjunction with those from the neuro-imaging studies. Once the surgery plan was finalized, these patients underwent the second stage of surgery to remove the electrode array and all epileptogenic brain areas. For patients undergoing one-stage epilepsy surgery, optical imaging acquisition was also performed prior to the confirmatory ECoG study, which was performed to identify the resection margin.

Neurologists analyzed all ECoG data and provided information on the localization of eloquent and epileptic cortical areas based on all neuro-imaging results. Eloquent areas are defined as cortical areas consistently related to a given function; e.g., sensory or motor. Epileptogenic cortex is considered an area of cortex that is required for seizure onset. Areas generating inter-ictal spikes and discharges are also generally considered epileptic. DIOSI data analyses in the previous section were conducted without any knowledge of the results of the ECoG study. Later, the ECoG study results and the actual area of surgical resection were used as gold standards to define the epileptogenic and eloquent cortical areas.

All optical data analyses were performed with MATLAB™ programs developed in-house following the steps shown in FIG. 1A. Images from both cameras were co-registered and cropped to show the same exposed cortex area at two wavelengths and smoothed using a filter with a 3-by-3 square window. A time series for each pixel $R(x,y,t)$ was analyzed, both in the time domain and the frequency domain. Since LFOs were of interest for this study, time series $R(p,t)$, where $p=(x,y)$, was filtered using a band-pass FIR filter (~0.02-0.1 Hz) which yielded $R_{low}(p,t)$. The FIR filter was designed in MATLAB™ using the Filter Design and Analysis Tool (fdatool) with an order less than a third of the data length. The artifacts in $R_{low}(p,t)$ originating from the light source and vessel movements were removed using a principal component analysis (PCA) method, which produced $R_{PCA}(p,t)$. A power spectral density map (SDM, ~0.02-0.1 Hz) was generated using $R_{pca}(p,t)$ at each wavelength. A correlation coefficient map (CCM) was created by calculating the extent of correlation between $R_{pca}(p,t)$ at 500 nm and 700 nm for each pixel. Pixels displaying negative correlations were extracted from the CCM. Only those spatially-connected pixel groups were included in the following analyses. To remove those isolated pixels showing negative correlations, MATLAB™ function "bwconncomp" was used with an arbitrary threshold of 25 pixels to identify those spatially-connected pixel groups. These pixels were subsequently classified via a mean shift clustering method into multiple clusters based upon their temporal profiles in $R_{pca}(p,t)$ at both wavelengths. This classification was performed with no a priori knowledge about the number of existing clusters. $R_{pca}(p,t)$ in each cluster was then denoted as $R_{ci}(p,t)$, where subscript i stands for the cluster number.

To understand effective connectivity in these clusters, a Granger causality toolbox for non-stationary signals was applied to the mean values of $R_{ci}(p,t)$ at 500 nm ($\overline{R_{ci}}(p,t)$) as shown in FIG. 1B. Influences that originated in a certain region and were imposed on others were labeled "directed influences," since this effect flowed in a specific direction. If $\overline{R_{ci}}(p,t)$ from region A was found to have a directed influence on the $\overline{R_{ci}}(p,t)$ of region B, region A would be denoted a Granger-cause (G-cause), while region B would be considered a Granger-effect (G-effect). When the directions of influence were identified, time series $\overline{R_{ci}}(p,t)$ at the G-causes and G-effects were used as a reference (i.e., seed) to calculate the seed-based correlation coefficients with $R_{pca}(p,t)$ from the other pixels within the field of view (FOV) at each wavelength, thereby demonstrating functional brain connectivity.

Based on the optical absorption spectra of oxy- and deoxy-hemoglobin, DIOSI data at 500 nm primarily reflect changes in cerebral blood volume (CBV). DIOSI data at 700 nm, on the other hand, are highly sensitive to hemoglobin oxygenation, because of the significant difference in the absorption coefficients between oxy- and deoxy-hemoglobin at this wavelength. Since both parameters are known to be affected by neuronal activity according to the Balloon model (Buxton 2012), investigating the relationship between the DIOSI data at 500 nm and 700 nm provided insights into the interplay between changes in CBV and oxygenation under the influence of both neuronal activity and metabolism. This, in turn, could offer a window of opportunity to separate epileptogenic from eloquent cortex using parameters that characterize the interplay between changes in CBV and oxygenation, as outlined in FIG. 1C. To verify this hypothesis, $\overline{R_{ci}}(p,t)$ at both wavelengths with negative correlations from epileptogenic and eloquent cortical areas, as defined by the outcomes of the ECoG studies, were applied to an autoregressive model with an exogenous source (ARX) expressed as:

$$y_t = \phi_0 + \sum_{i=1}^{p} \phi_i y_{t-i} + \sum_{i=1}^{r} \psi_i u_{t-i} + \varepsilon_t, \quad (1)$$

where u is $\overline{R_{ci}}(p,t)$ at 500 nm (related to CBV) as the exogenous source (input of the system), y is $\overline{R_{ci}}(p,t)$ at 700 nm (reflecting variations in oxygenation) as the output of this stochastic system, $\Phi$ and $\psi$ are the coefficients for variables y and u, respectively, p and r are the order of the series for y and u, respectively, and $\varepsilon$ is white noise. Theoretically, by calculating $\Phi$ and $\psi$, changes in oxygenation could be predicted from this ARX model, if the changes in CBV were known. Although this data-driven model did not strictly follow any biophysics-based mechanism, the impulse response functions (IRFs) of the model, to a certain extent, could indirectly indicate the relationship between changes in CBV and oxygenation, and hence contain useful features to differentiate eloquent from epileptogenic cortex. The concept behind the IRFs of this ARX model is similar to the hemodynamic response function used in event-related fMRI analysis (Glover 1999).

A support vector machine (SVM), a common machine-learning method that is frequently used in predictive modeling for clinical decision-making, was employed with quadratic programming to train the computer to identify the differences between the IRFs obtained from epileptogenic and eloquent cortical areas. SVM has primarily been employed in EEG analysis for seizure detection (Guo et al., 2010, Subasi et al., 2010 and Zavar et al., 2011). However, it has also been used as a diagnostic tool in anatomical and functional imaging studies (Chaplot et al., 2006, El-Naqa et al., 2002 and Ramirez et al., 2013). Here, $\overline{R_{ci}}(p,t)$ obtained from the epileptogenic and eloquent cortical areas were split into two parts: one was used as the training data set and the other as a testing data set. Each part was about 100 seconds long. Upon obtaining the estimated IRFs from each data set, Haar wavelet decomposition (Mallat 1989) was employed to extract unique features from IRFs. The coefficients obtained from the Haar wavelet decomposition were scaled (i.e., standard deviation=1) and centered (i.e., mean=0). Coefficients were used in the SVM as the features for training and testing purposes, if they were found to be significantly different between two groups of data using the non-parametric permutation test (refer to section 2.6.1). Finally, the performance of the SVM with different orders of ARX model (p and r: 5-40) was empirically assessed in terms of its accuracy, sensitivity, specificity, and area under the receiver operating characteristic (ROC) curve.

Eleven patients undergoing epilepsy surgery were enrolled in this study, and their individual demographic and clinical information, such as post-surgery outcome, are provided in Table 1. It should be noted that post-surgery outcomes were not affected by any of the DIOSI studies being presented. Some patients (Patients 1, 5, and 7) were not completely seizure free after surgery, which could be due to incomplete resections of the lesion and electrographically-abnormal region (Paolicchi et al., 2000, Krsek et al., 2013) or insufficient pre-operative mapping of multi-focal lesions and/or epileptogenesis (Krsek et al., 2013). However, the results from these three patients were retain for analysis, since the ECoG analyses performed on these patients did succeed at locating the seizure-onset zones within the operative sites. The DIOSI study was performed twice in three of these patients (Patients 2, 4 and 7); each of these two studies possessed a unique view angle to the exposed cortex. Therefore, the analysis results from a total of fourteen image sequence sets are presented.

TABLE 1

Individual demographic and clinical data on each of the eleven patients

| Patient | Gender | Age (y/o) | Stage | Craniotomy | Pathology | Follow-up duration (months) | Post-surgery outcome |
|---|---|---|---|---|---|---|---|
| 1 | Male | 14 | 2 | L F P | Tuberous sclerosis | 18 | No improvement. Still having seizures. |
| 2 | Female | 17 | 2 | R F T | FCD | 12 | No seizures |
| 3 | Female | 7 | 2 | R | Type 2A FCD | 31 | Had auras. Now seizure free. |
| 4 | Male | 12 | 2 | L | n/a | 9 | No seizures |
| 5 | Male | 16 | 2 | R F T | Rasmussen encephalitis | 32 | Initially seizure free, now having seizures |
| 6 | Female | 13 | 2 | L F P T | Cavernous malformation | n/a | n/a |
| 7 | Female | 15 | 2 | L F T | Type 2A | 18 | No disabling |

TABLE 1-continued

Individual demographic and clinical data on each of the eleven patients

| Patient | Gender | Age (y/o) | Stage | Craniotomy | Pathology | Follow-up duration (months) | Post-surgery outcome |
|---|---|---|---|---|---|---|---|
|  |  |  |  |  | FCD; mild hippocampal gliosis |  | seizures. Seizure-free except for 2-3 seizures when anti-epileptic drugs stopped. |
| 8 | Male | 8 | 2 | L T | Cellular glial tumor; favor FCD | n/a | n/a |
| 9 | Male | 9 | 2 | R F T | Type 2A FCD | 18 | No seizures |
| 10 | Female | 12 | 2 | L T O | Gliosis | 28 | No seizures |
| 11 | Male | 2 months | 1 | R F T | FCD | 24 | No seizures | y/o: years old; L: Left; R: Right; F: Frontal; T: Temporal; O: Occipital; P: Parietal; FCD: Focal cortical dysplasia; n/a: not available.

Figure 2A:
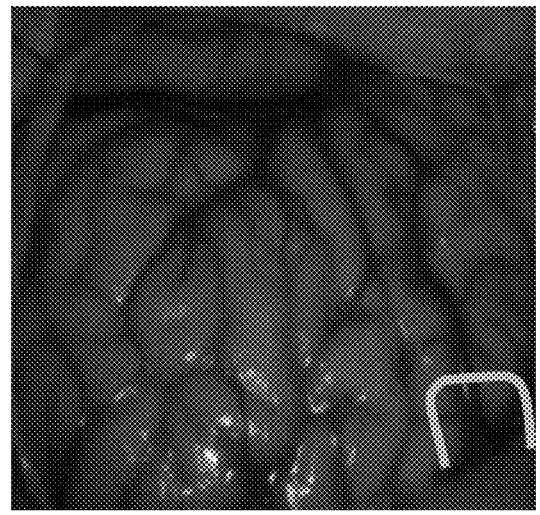
FIG. 2A is an image of a brain captured at 700 nm using a dynamic intrinsic optical signal imaging (DIOSI) system according to an embodiment of the present invention, wherein the resection area is outlined.
Figure 2B:
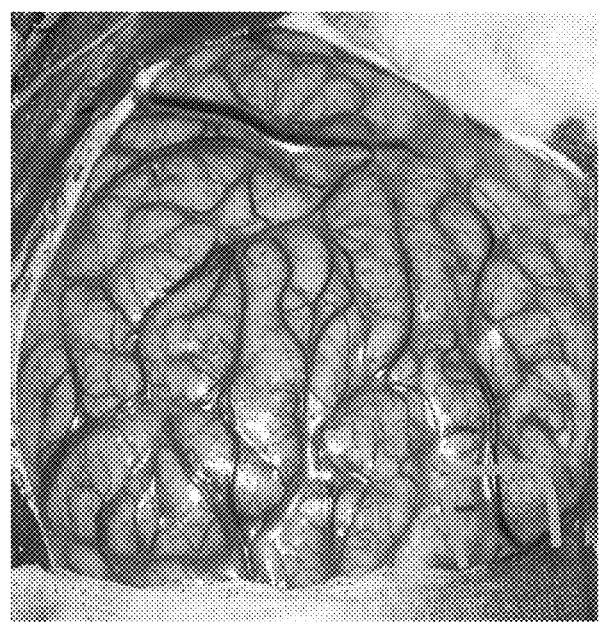
FIG. 2B is an image of a brain captured using a dSLR camera, wherein the resection area outlined.
Figure 2C:
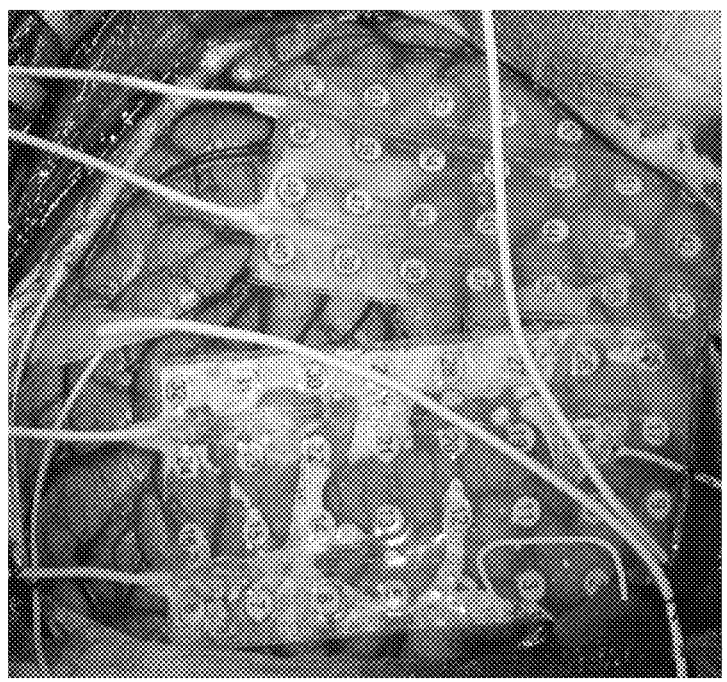
FIG. 2C is an image of an exposed cortical surface with an ECoG electrode array in place.
Figure 2D:
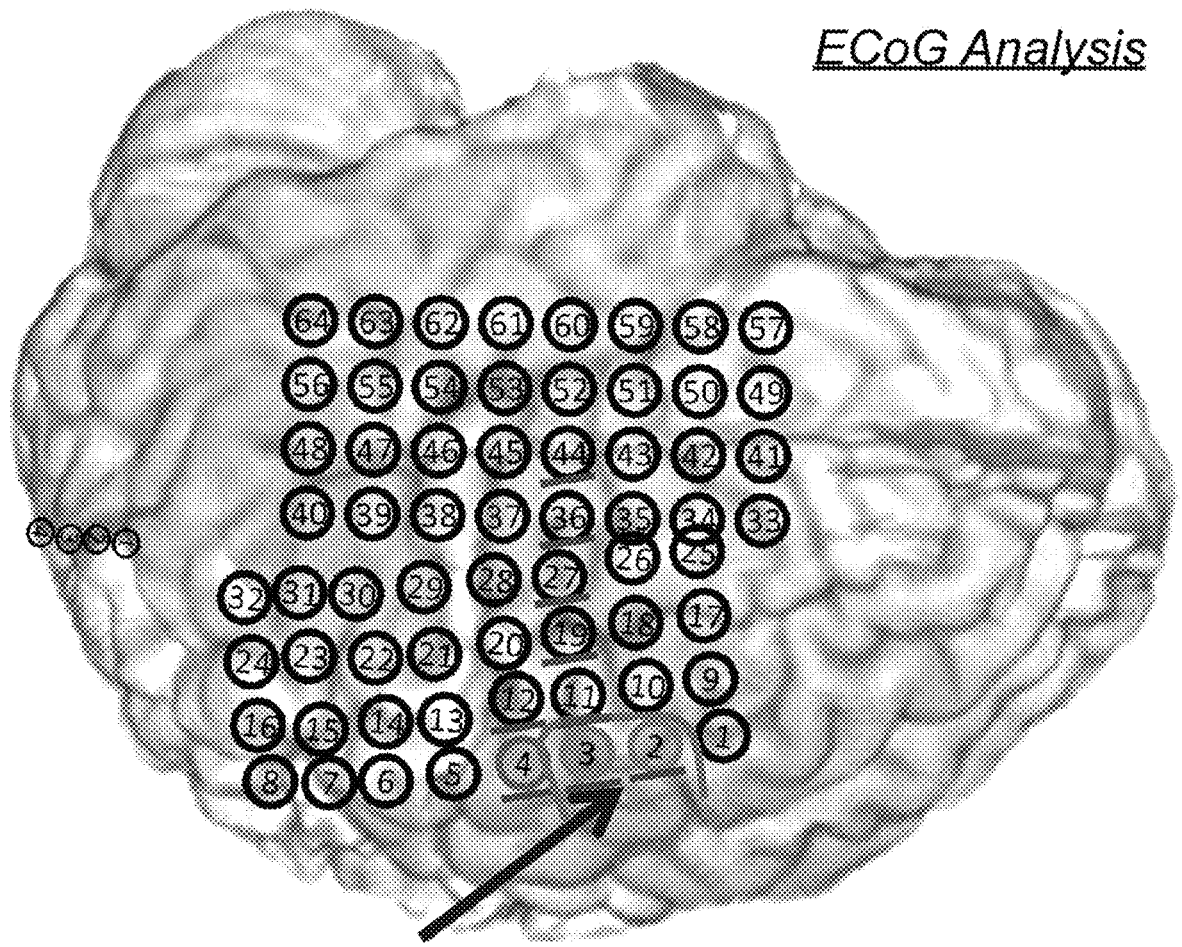
FIG. 2D is a schematic diagram showing the location of epileptic and eloquent cortical areas as determined by neurologists using ECoG electrode numbers.

FIGS. 2A-2D were taken from Patient 1. FIG. 2A is an image acquired with a DIOSI system at 700 nm with a resection area outlined. FIG. 2B is an image captured using a commercial-grade digital camera with the resection area outlined. Following DIOSI image acquisition, another picture of the exposed cortical surface was taken with the ECoG electrode array in place, as seen in FIG. 2C. As seen in FIG. 2D, Neurologists documented the locations of epileptic and eloquent cortical areas using the ECoG electrode numbers. The position of electrodes 2 and 3 was determined to be the surgical resection zone. Using images 2A-2D, the results derived from DIOSI data analyses according to an embodiment of the present invention could be compared with those of ECoG data analyses.

Figure 3A:
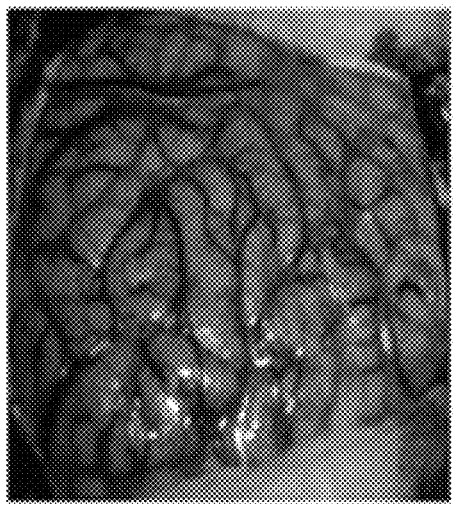
FIG. 3A is a raw image obtained by a dynamic intrinsic optical signal imaging (DIOSI) system at 500 nm.
Figure 3B:
FIG. 3B is a raw image obtained by a dynamic intrinsic optical signal imaging (DIOSI) system at 700 nm.
Figure 3C:
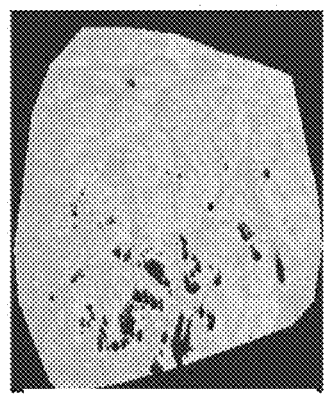
FIG. 3C is a spectral density map (SDM) at 500 nm showing the power of hemodynamic low-frequency oscillations (LFOs).
Figure 3E:
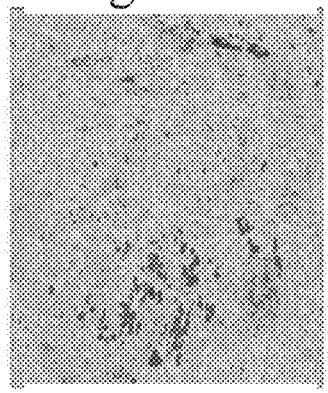
FIG. 3E is an image showing a correlation coefficient map (CCM) obtained by calculating the correlation coefficient between LFOs at both 500 nm and 700 nm wavelengths.
Figure 3D:
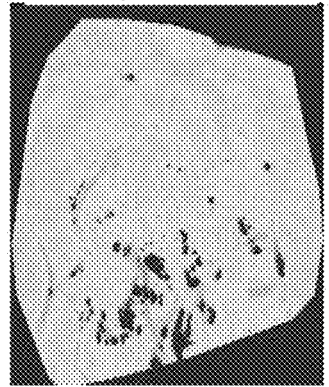
FIG. 3D is a spectral density map (SDM) at 700 nm showing the power of hemodynamic low-frequency oscillations (LFOs).
Figure 3F:
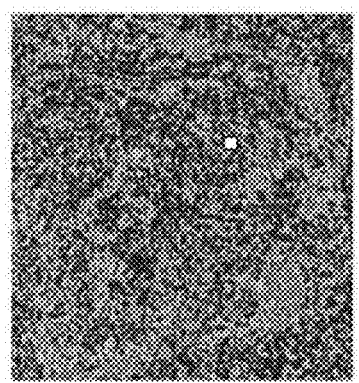
FIG. 3F is an image illustrating K-means segmentation performed to isolate regions with negative correlations according to an embedment of the present invention.
Figures 3G, 3H:
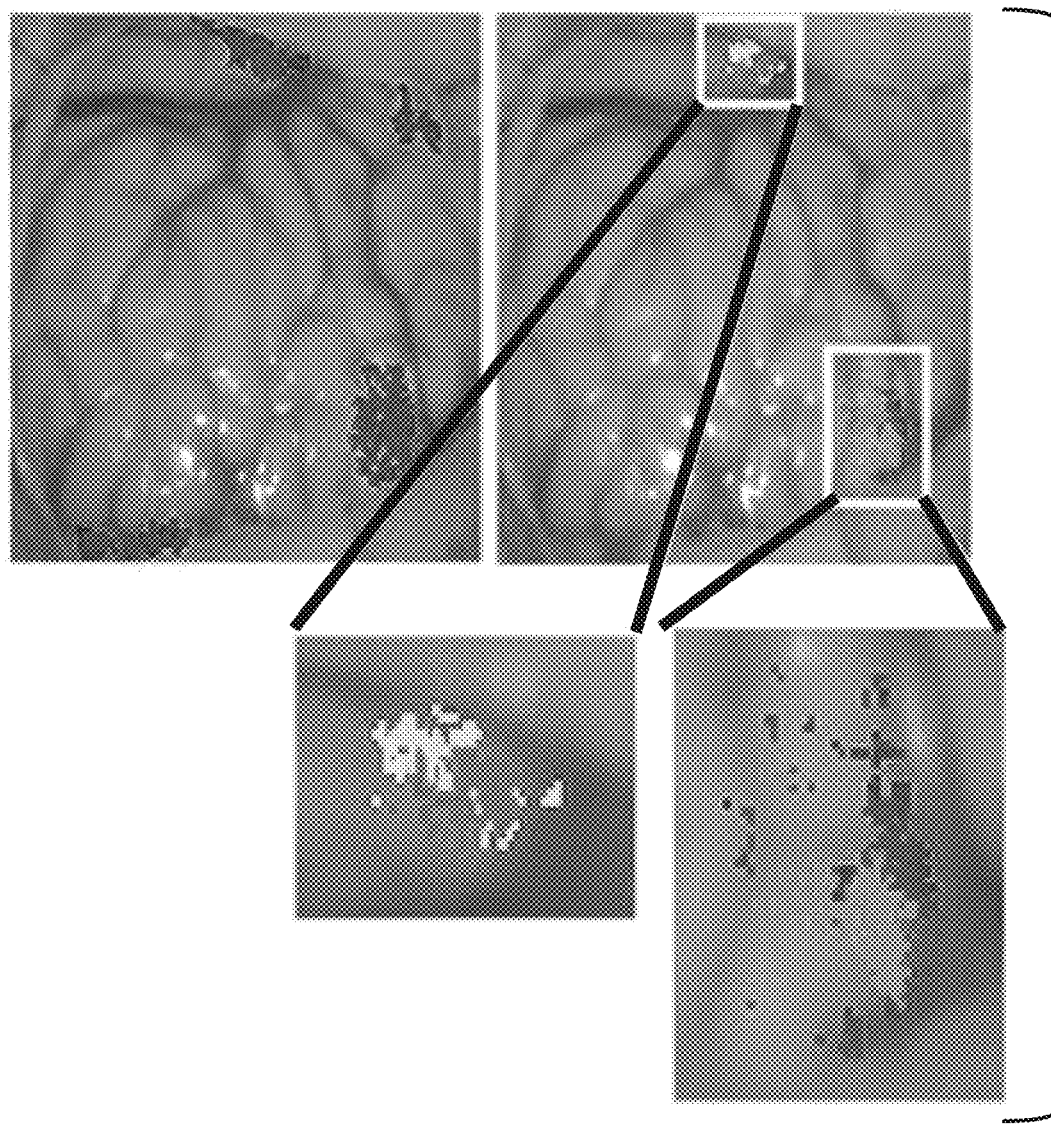
FIG. 3G is an image showing the isolation of regions with negative correlations.
FIG. 3H is an image showing the classifications of the clusters of FIG. 3G by mean shift clustering.
Figure 3I:
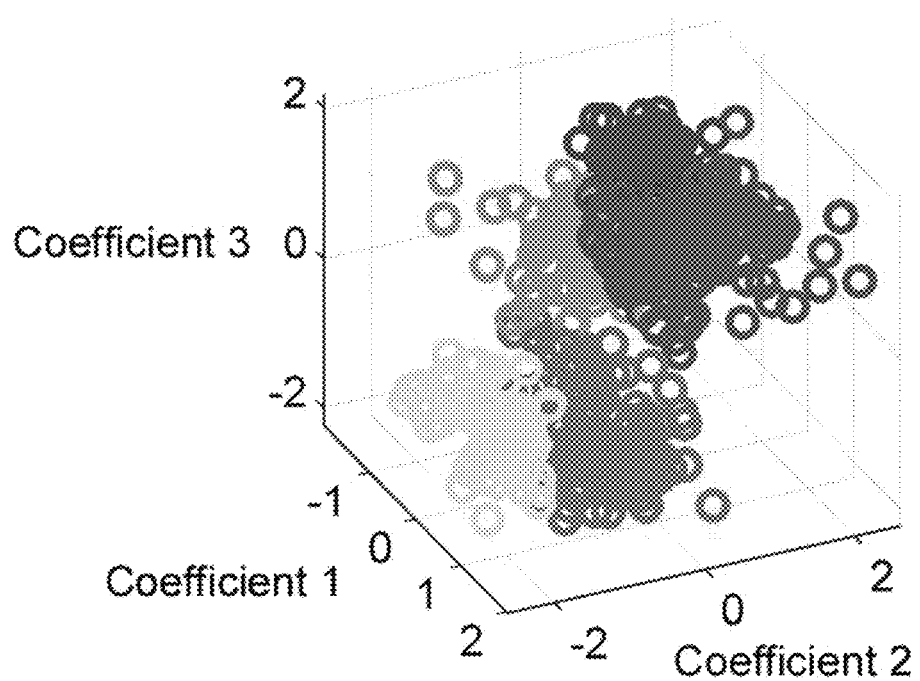
FIG. 3I is a 3-D scatter plot of clustering features.
Figure 3J:
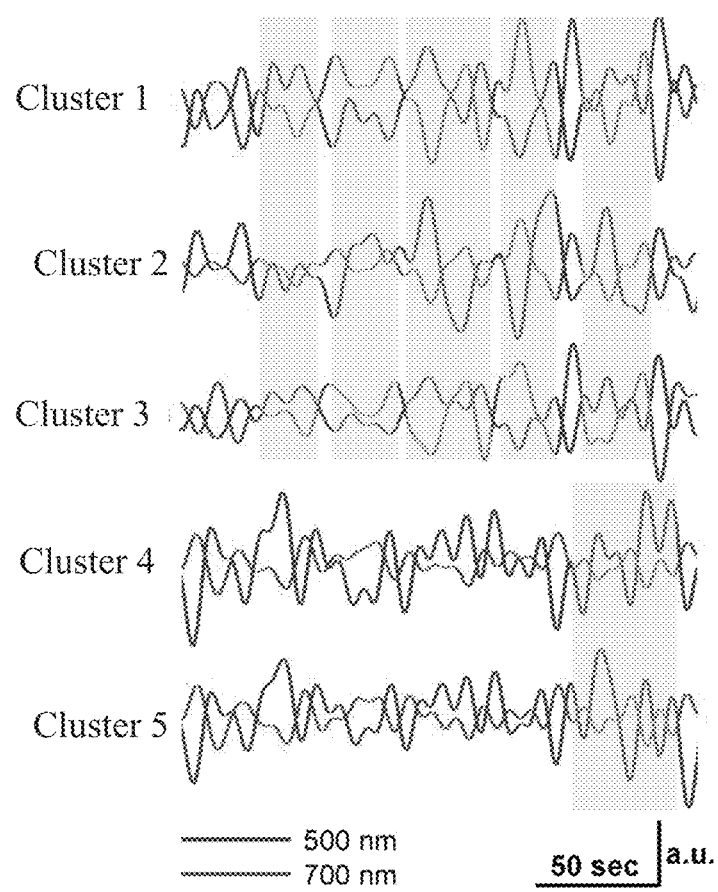
FIG. 3J includes graphs showing the unique temporal profiles of cluster demonstrating LFOs.
Figures 3N, 3O, 3P:
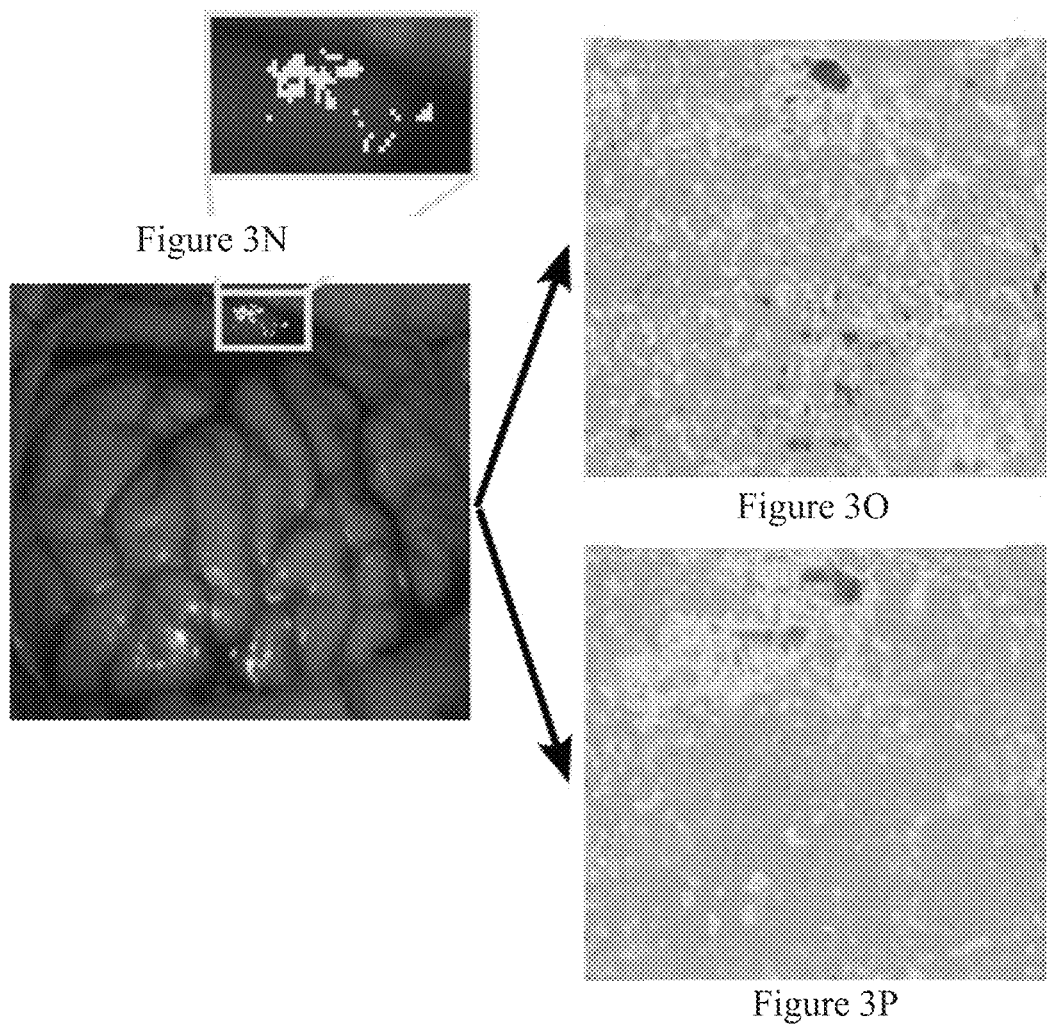
FIG. 3N is an image showing the identification of Granger-effects.
FIG. 3O is an image of a correlation coefficient map (CCM) for Granger-effects at 500 nm.
FIG. 3P is an image of a correlation coefficient map (CCM) for Granger-effects at 700 nm.
Figure 4A:
FIG. 4A is a raw image obtained by a dynamic intrinsic optical signal imaging (DIOSI) system at 500 nm with a resection area outlined.
Figure 4B:
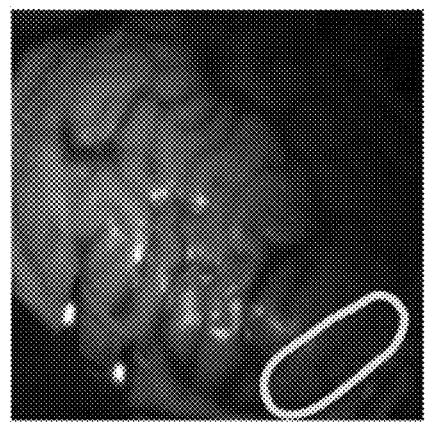
FIG. 4B is a raw image obtained by a dynamic intrinsic optical signal imaging (DIOSI) system at 700 nm with a resection area outlined.
Figure 4C:
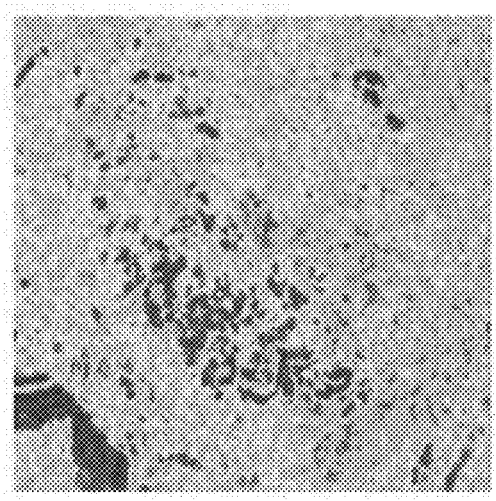
FIG. 4C is an image showing a correlation coefficient map (CCM) obtained by calculating the correlation coefficient between LFOs at both 500 nm and 700 nm wavelengths.
Figure 4D:
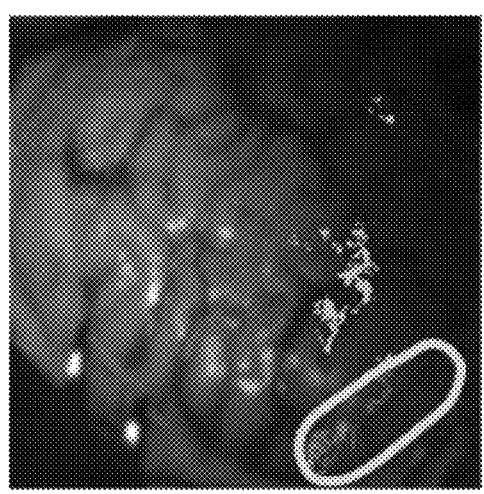
FIG. 4D is an image showing the classification of negatively correlated regions by mean shift clustering with the resection area outlined.
Figures 4I, 4J, 4K:
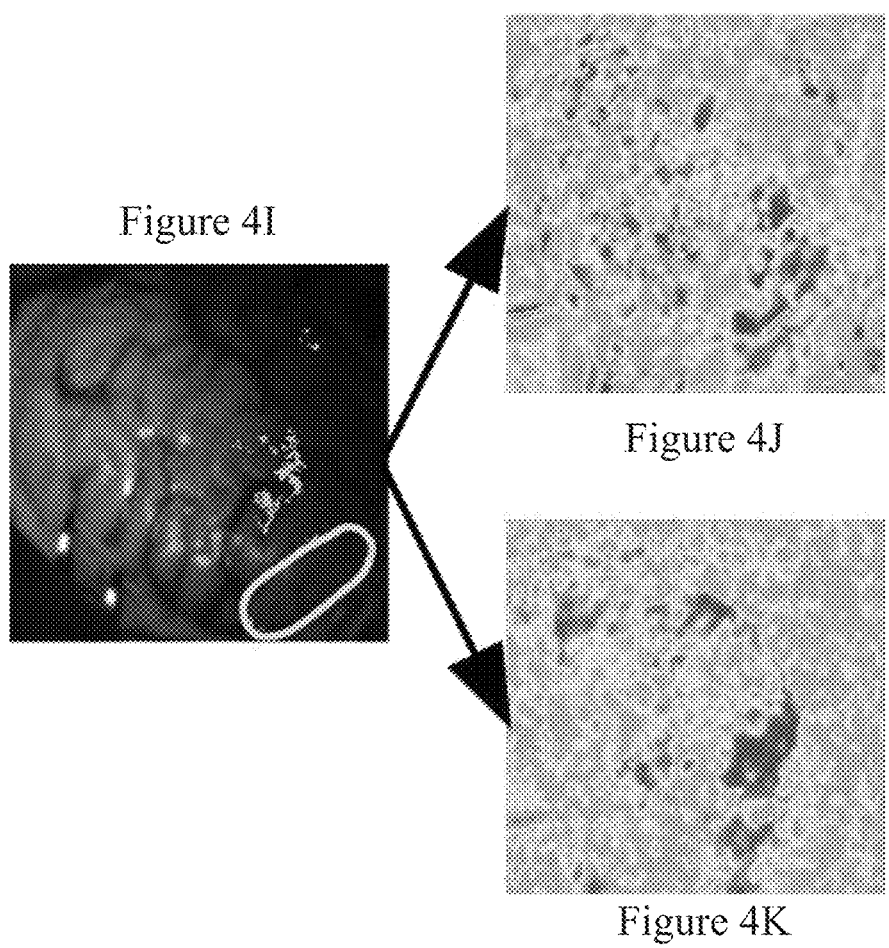
FIG. 4I is an image showing the identification of Granger-effects with the resection area outlined.
FIG. 4J is an image of a correlation coefficient map (CCM) for Granger-effects at 500 nm.
FIG. 4K is an image of a correlation coefficient map (CCM) for Granger-effects at 700 nm.
Figure 6A:
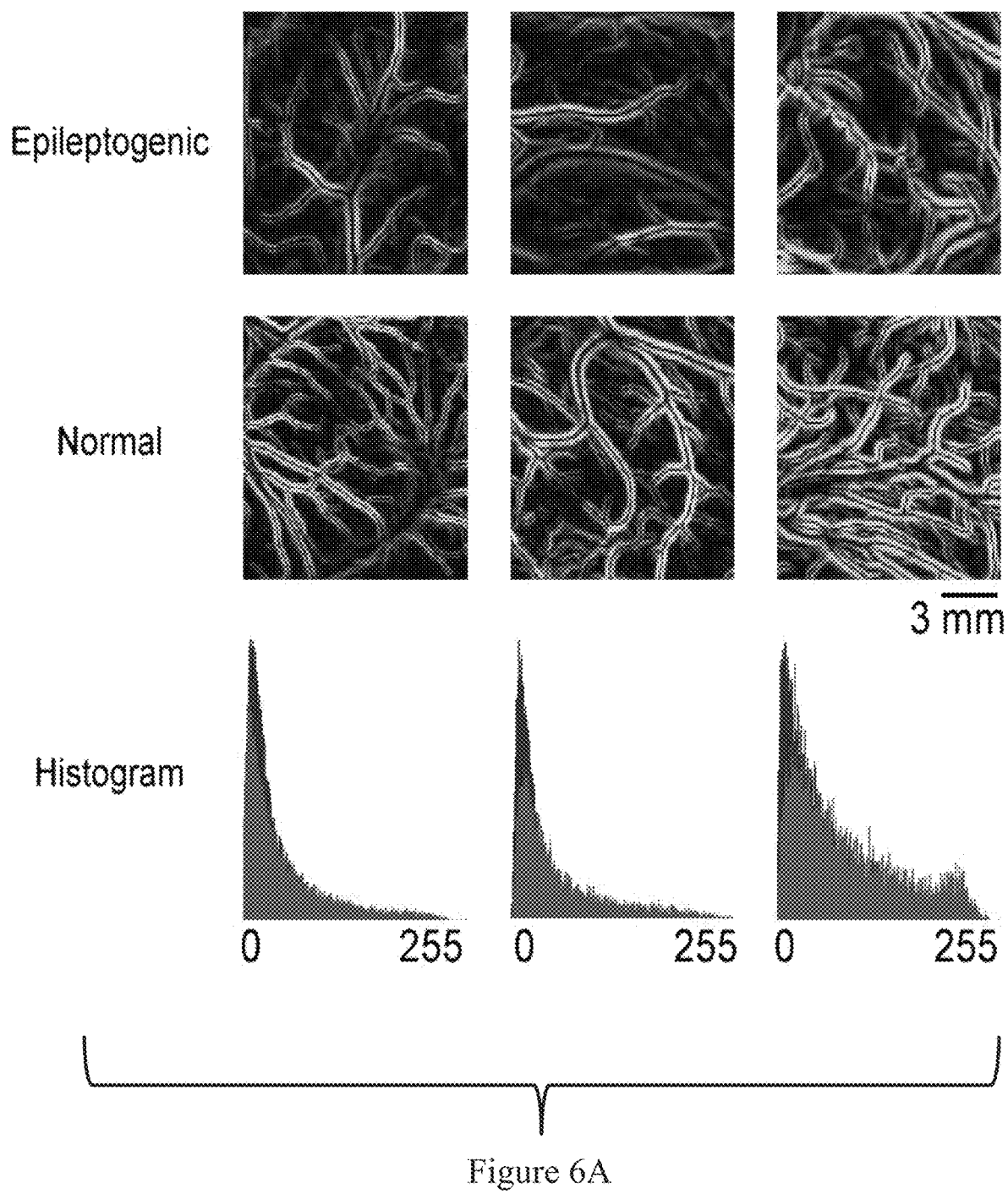
FIG. 6A includes images showing vascular abnormalities in the superficial layer (anatomical features) and their respective histograms.
Figure 6B:
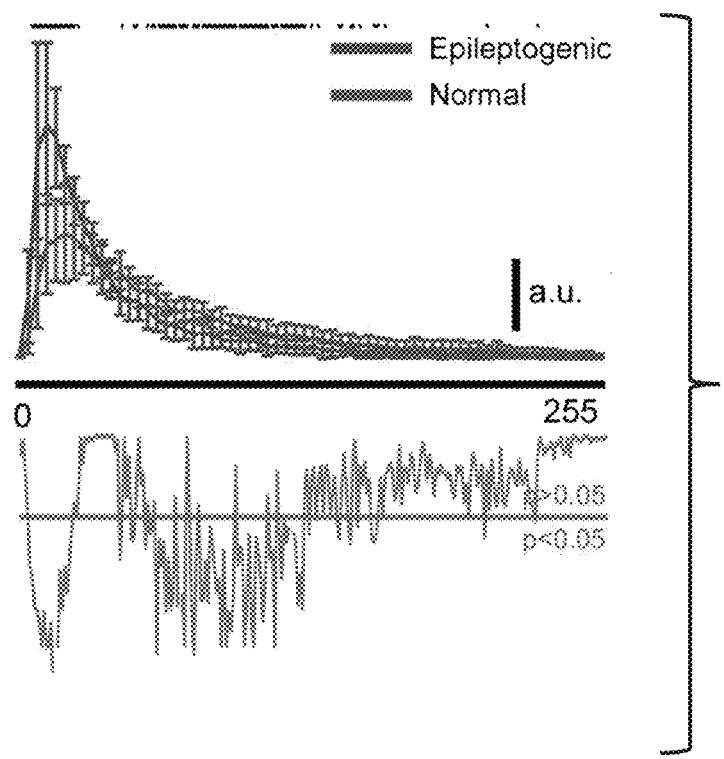
FIG. 6B is a normalized histogram of a vessel network image obtained from epileptogenic and normal cortices.

Consistent with the findings of Song et al. (2012), strong LFOs (<<0.1 Hz) were observed in all fourteen acquired data sets. A set of representative LFO analysis results from the same patient as FIGS. 2A-2D is presented in FIGS. 3A-3P. In this analysis, negative correlations between intrinsic optical signals at both wavelengths were located in certain focal areas as shown by the correlation coefficient map of FIG. 3E. Using k-means segmentation, negative-correlation areas greater than 100 pixels were separated from the remaining cortical areas (FIG. 3G). These areas included both epileptic cortex and normal eloquent areas. Intrinsic optical signals from these isolated areas were separated further into multiple clusters by simultaneously using the temporal features identified from both wavelengths (FIG. 3H). A 3-D scatter plot of the classified features is shown in FIG. 3I. Each cluster possessed a unique oscillation pattern (FIG. 3J), for which the spatial distribution could be scattered (FIG. 3H). As an example of the robustness of the classification process, Clusters 1, 2 and 3 in FIG. 3H are connected spatially, but the temporal profiles of their intrinsic optical signals at both wavelengths (FIG. 3J) are clearly different, as marked by boxes. The same conclusion can be drawn from Clusters 4 and 5, as well.

To understand effective connections between these epileptic and eloquent areas, the directed influences between them were identified using the Granger causality method. In general, the clusters located inside the resection area, presumed to be related to seizure onset, were found to exert influences on other brain areas, as seen in FIG. 3K. However, not all the identified clusters exhibited causal relationships (e.g., Clusters 1, 2, and 4 in FIG. 3H), which might indicate that these areas were not effectively connected, regardless of their structural or functional connections. Once all the G-causes and G-effects were determined, the averaged intrinsic optical signals $\overline{R}_{ct}(p,t)$ within a G-cause area and a G-effect area were used as the seeds to obtain a CCM based on seed-based correlations with intrinsic optical signals of all the other pixels $R_{pca}(p,t)$ at the corresponding wavelengths. It is clear that the correlated areas revealed at 500 nm (FIGS. 3L and 3O) were much more focal than those at 700 nm (FIGS. 3M and 3P), which could result from the longer optical path length for biological tissue at 700 nm.

FIG. 4 shows representative results from another studied patient (Patient 2) as a further example, and leads to similar conclusions with regards to the importance of LFO clustering, as well as the need to investigate effective connectivity. Unlike Patient 1 in FIG. 3, the G-cause (FIG. 4F) and G-effect (FIG. 4I) of Patient 2 seem to be temporally correlated (FIGS. 4G, 4H, 4J and 4K). However, the Granger causality test indicated a difference between these two areas. Once again, the G-cause area is located inside the outline resection zone, outlined in FIG. 4F, and is responsible for seizure onset in Patient 2.

Among all fourteen imaging data sets, there were two cases (Patients 6 and 10) in which only eloquent areas were identified within the optical field of view (FOV). For these two cases, the resection areas were either below the cortical surface or adjacent to the craniotomy but covered by the skull. Nevertheless, strong hemodynamic LFOs were found within the resection areas (i.e., epileptogenic areas) in all the remaining twelve cases. Seventy-five percent of the resection areas exhibited negative correlations between their intrinsic optical signals at 500 nm and 700 nm, and they had directed influences on other cortical areas. Meanwhile, 83% of the G-causes identified via the Granger causality method were related to epileptic activity (i.e., either ictal or interictal discharges), as shown in FIG. 5A. However, eloquent areas could be the G-cause as well, as on some occasions they either directly contributed to the activities in a distant cortex (both data sets of Patient 7) or relayed the activities from the epileptic cortex to some distant cortex (Patients 3 and 5, and both data sets of Patient 4). This indicates that eloquent cortical areas, if involved, may facilitate the propagation of epileptic activities through their network to remote cortical areas.

Figure 7A:
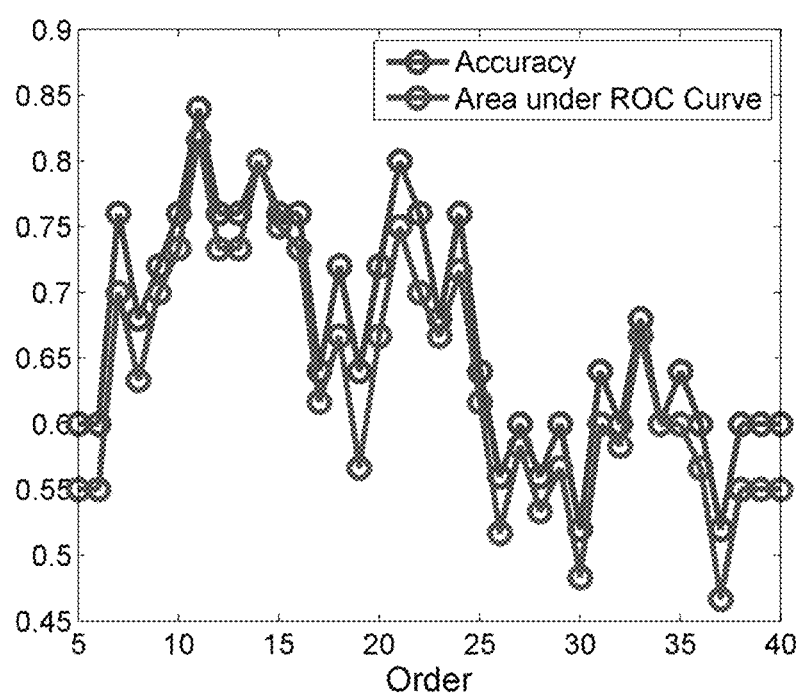
FIG. 7A-7C show the differentiation between epileptogenic and eloquent cortex based on functional features of vascular networks.
Figure 7B:
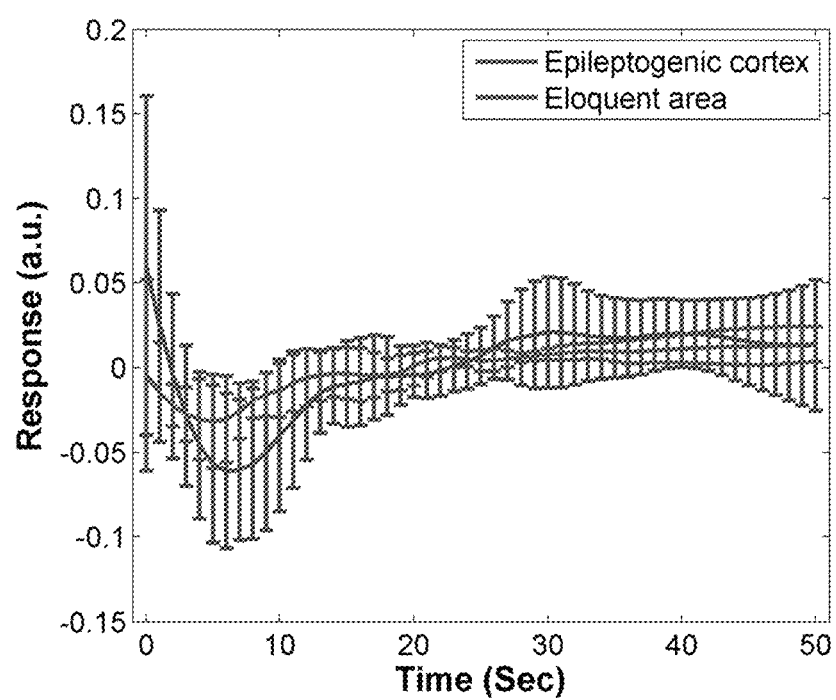
Figure 7C:
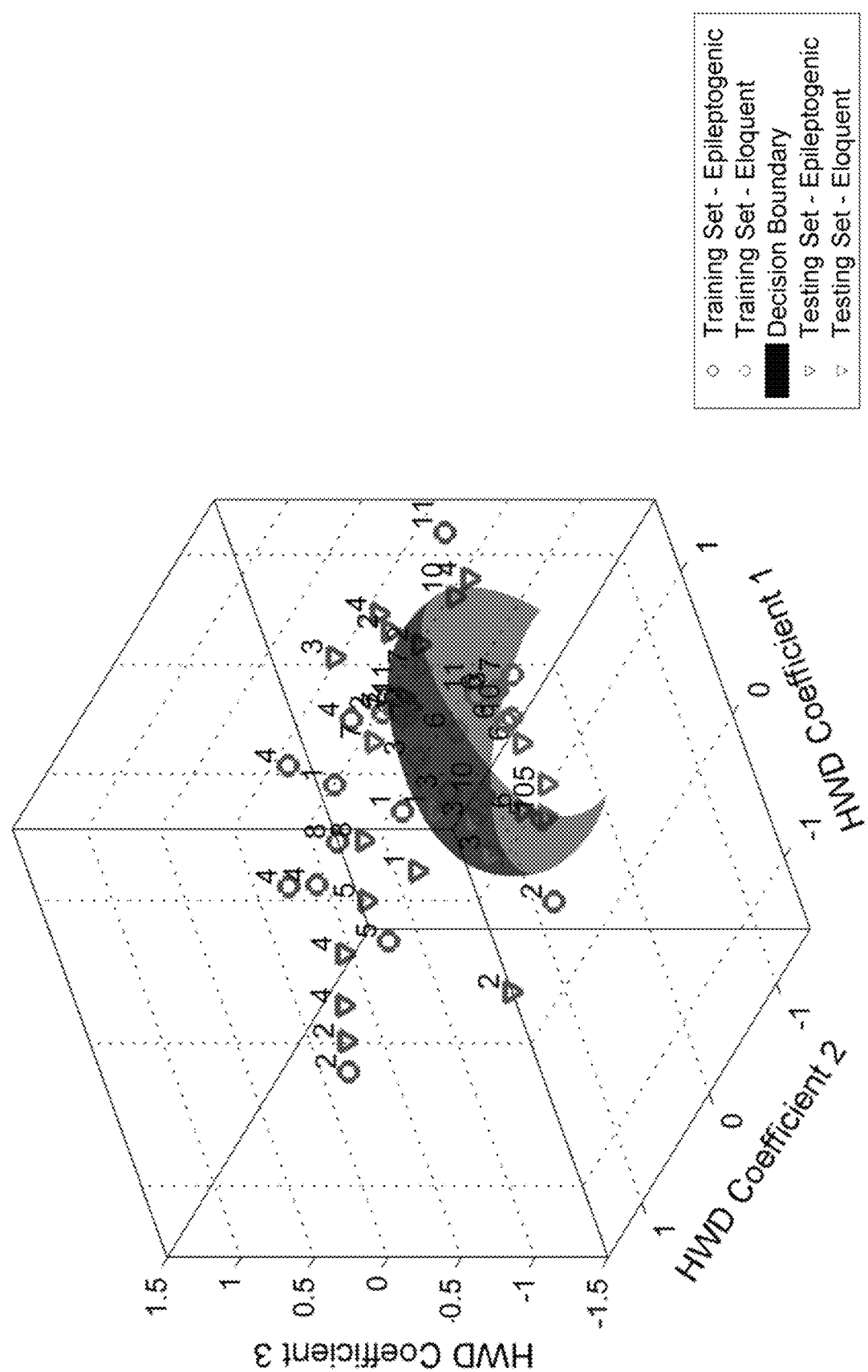
Figure 8A:
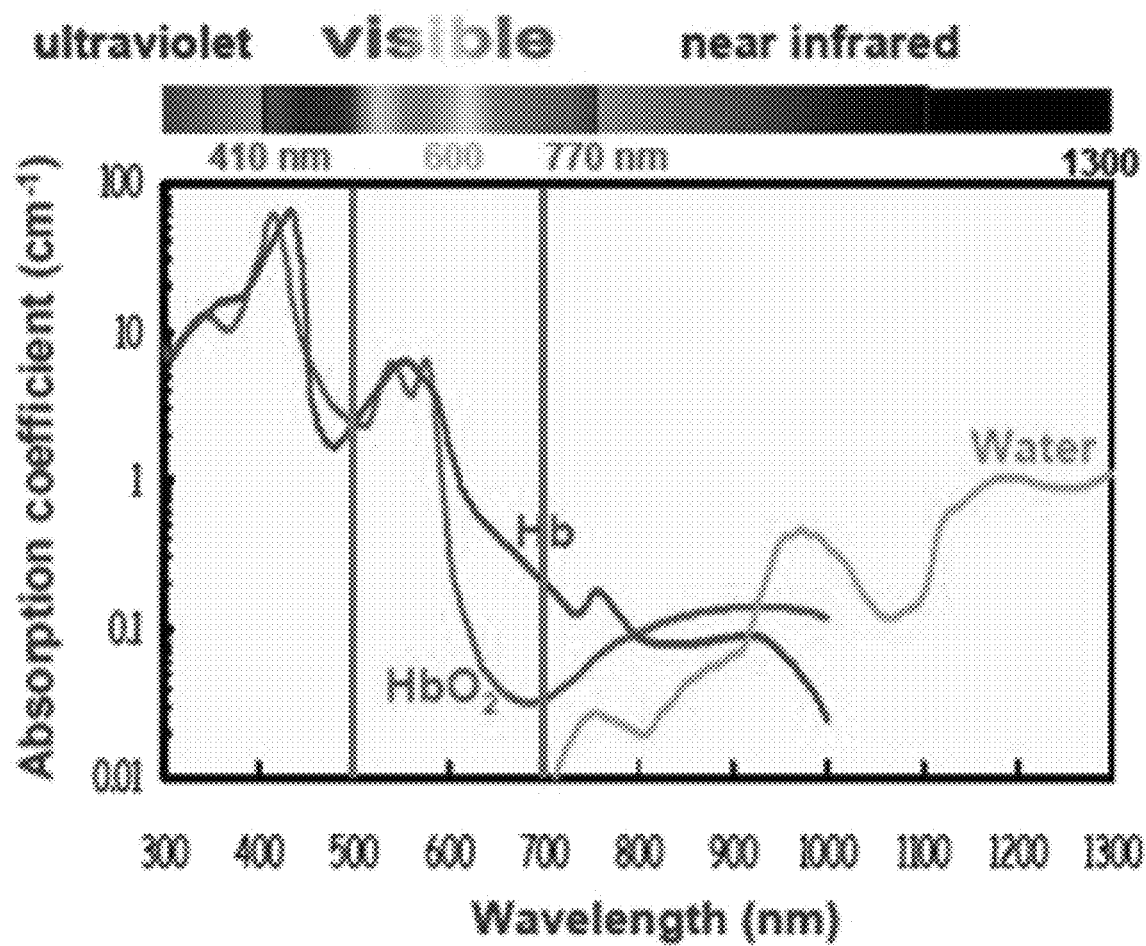
FIG. 8A is a graph illustrating the absorption spectra of deoxy-hemoglobin (Hb), oxyhemoglobin ($HbO_2$), and water.
Figure 8B:
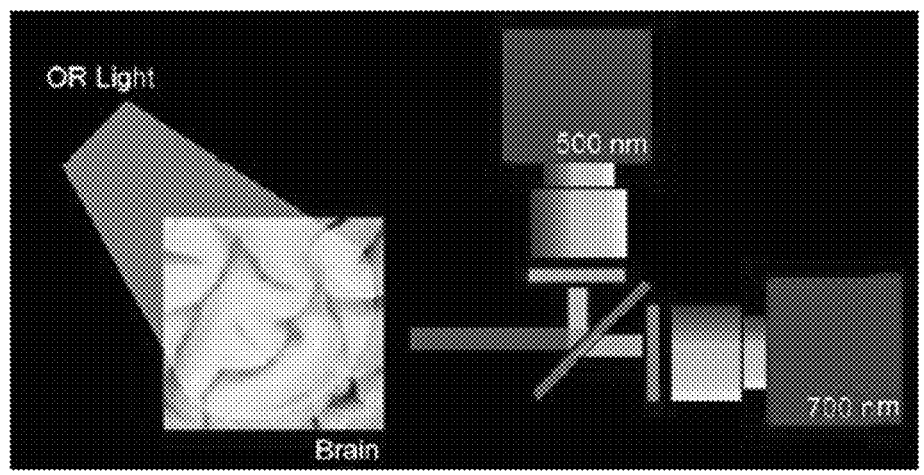
FIG. 8B illustrates a dynamic intrinsic optical signal imaging (DIOSI) system according to an embodiment of the present invention.
Figure 9:
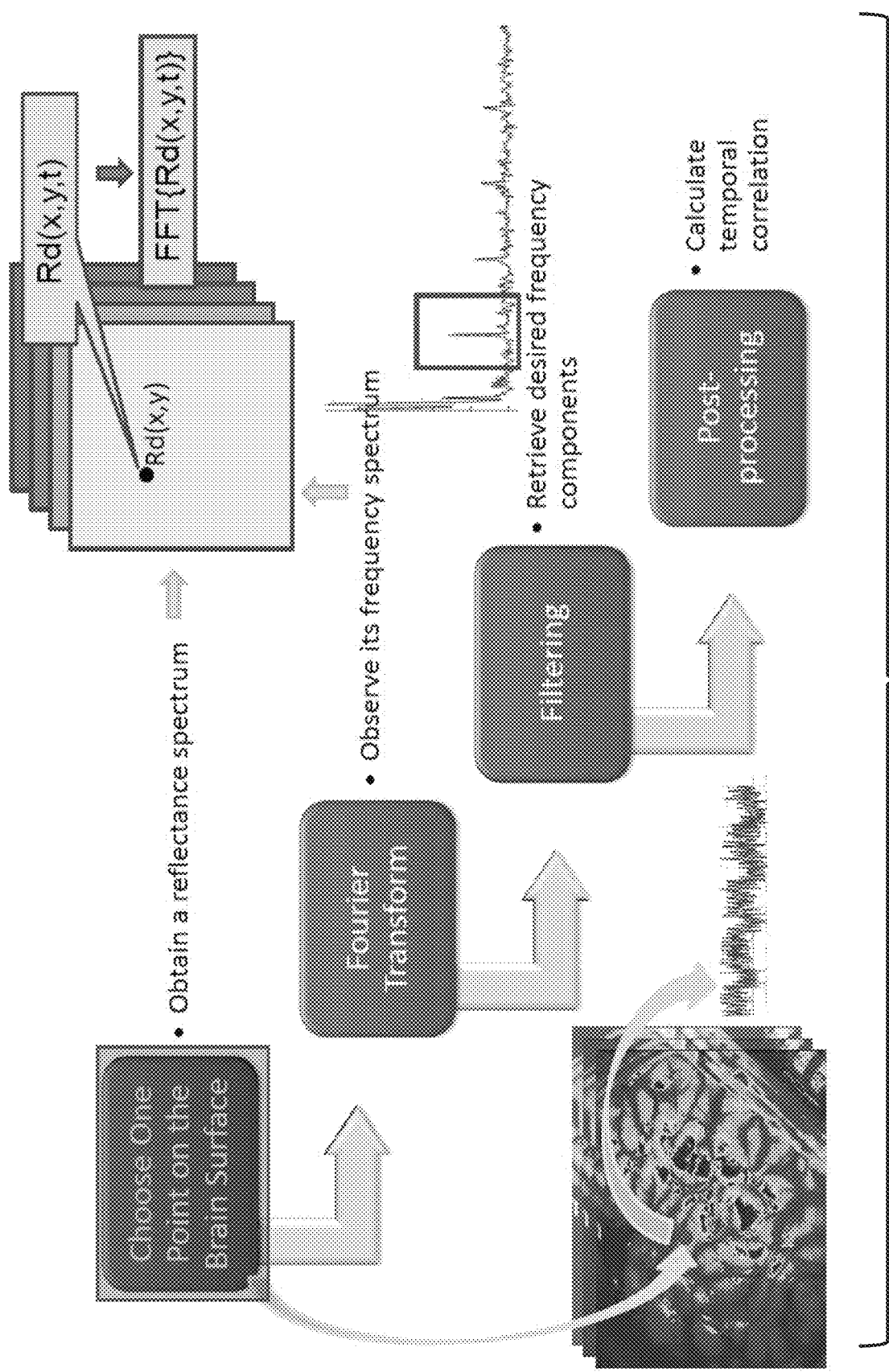
FIG. 9 is a flow chart illustrating a method for identifying epileptogenic tissue according to an embodiment of the present invention.

Intrinsic optical signals at 500 nm represent variations in CBV, while signals at 700 nm primarily reflect changes in oxygenation. In this study, the coupling mechanism between the change in CBV and that in oxygenation was investigated using an ARX model, wherein variations in oxygenation were considered output signals and those for CBV were treated as inputs. The IRFs obtained from the ARX model were capable of directly demonstrating the coupling mechanism between CBV and oxygenation. IRFs from the epileptogenic cortex and eloquent cortex appeared to be different in their temporal profiles. However, there was no statistically-significant difference between the amplitudes of IRFs obtained from the epileptogenic and eloquent cortical areas (FIG. 7B). The training and testing data sets for the SVM classifier were extracted from the same recordings of each patient, but at different times. The SVM was applied to the training data sets to identify a hyper-plane that could identify differences between the IRFs obtained from epileptogenic (n=15) versus eloquent areas (n=10). Subsequently, the accuracy of differentiation was evaluated by applying the same SVM model to the testing data set. The accuracies of SVM models with ARX models of different orders (5-40) were compared and are illustrated in FIG. 7A. The ARX model at order 11 yielded the highest accuracy (84%) and the largest area under the ROC curve (0.82 out of 1) in SVM. An optimal hyper-plane in SVM was observed that was able to separate the IRFs of the epileptogenic cortical areas from those of the eloquent areas with a sensitivity of 93% and specificity of 70% (FIG. 7C).

In the present example, the hemodynamic LFOs observed from the DIOSI recordings were an important biomarker differentiating epileptogenic cortex from normal eloquent areas. In addition, a significant difference between the vessel networks in epileptogenic cortex and normal brain area was identified. The differentiation methodology of this example involving LFOs relies neither on seizure attacks to localize epileptogenic cortex, nor on any external stimulation to map eloquent areas. Instead, it emphasizes the effective connectivity between various cortical regions, vessel network structures, and biophysical connections between changes in local blood volume and oxygenation. The feasibility of using this methodology for intraoperative guidance was evaluated using an SVM classifier to discriminate between epileptogenic and eloquent cortex.

The physiological signals centered in the in vivo study are low-frequency, spontaneous, hemodynamic oscillations (<<0.1 Hz). In the present study, LFOs tended to be local and their localizations were very reproducible from different observations, appearing in eloquent as well as epileptogenic cortical areas. Sophisticated data analysis schemes were employed to differentiate between the LFOs originating in eloquent cortex and those from epileptogenic cortex. The methodology of this example was used to identify differences in resting-state hemodynamic LFOs between the eloquent and epileptogenic cortical areas, in terms of brain connectivity and underlying biophysical mechanisms. Instead of relying solely on the magnitudes of LFOs (Song et al., 2012), the negative correlation between the DIOSI data at 500 nm and 700 nm was taken as an indication of underlying neuronal activity, which could be explained by the generally-accepted balloon model (Buxton et al., 2004 and Buxton 2012). For each case studied, epileptogenic cortex predominantly had directed influences on no less than one area, sometimes in close proximity and sometimes remote, probably because of different propagation mechanisms for the epileptiform discharges. Such connections were further investigated using the G-cause as the reference in seed-based spatial correlation analysis, which provides insights into the network in a global view and the different underlying phenomena in the DIOSI data.

The ARX modeling employed in the methodology of this example was adopted to identify those unique temporal variations in hemodynamics that occur in epileptogenic cortex during non-ictal periods. SVM based upon the outcome of the ARX modeling was very accurate at differentiating epileptogenic cortex from eloquent cortical areas. This success may be attributed to alterations in the vasculature network, as well as to neurovascular/neurometabolic couplings within the epileptogenic cortex. DIOSI at 500 nm is predominantly used to measure changes in CBV, modulated by activity-evoked dilation of the pial arterioles (Lavine et al., 2011). On the other hand, DIOSI at 700 nm is sensitive to variations in the oxygen content of blood within the venous network (Lavine et al., 2011). Through ARX modeling of both DIOSI signals, the dynamic interplay between the arteriolar and venous networks (i.e., vasculature characteristics) was examined. The same approach should also reveal regional neuro-activity and neuro-metabolism, because of the neurovascular and neurometabolic coupling mechanisms that exist within the capillary bed that forms the bridge between the arteriolar and venous networks.

In this example, a new methodology of intraoperative optical imaging was investigated to detect and differentiate epileptogenic from eloquent cortex in pediatric patients with focal epilepsy. The methodology was based on the effective connectivity, underlying biophysical mechanisms, and vasculature network characteristics of the cortical surface. Together, this creates a new means of intraoperative epileptogenic cortex localization that is both economical and effective. More importantly, this analysis based on biophysical mechanisms can differentiate between eloquent and epileptogenic cortex with high sensitivity and specificity. Neither external stimulation nor reduced anesthesia is required, both of which are required for current intraoperative monitoring techniques. More importantly, the analytical methods in this applicaton can be applied to data obtained from simultaneous BOLD- and VASO-fMRI, as well as from other non-invasive optical imaging modalities capable of acquiring hemodynamic LFOs from the brain.

The subject invention includes, but is not limited to, the following exemplified embodiments.

Embodiment 1

A method for identifying epileptogenic cortices in a brain, the method comprising determining areas of the brain that are experiencing hemodynamic low frequency oscillations.

Embodiment 2

The method according to embodiment 1, wherein the determining areas of the brain that are experiencing hemodynamic low frequency oscillations comprises detecting cerebral blood volume low frequency oscillations and detecting blood oxygenation low frequency oscillations.

Embodiment 3

The method according to any of embodiments 1-2, wherein the measuring hemodynamic low frequency oscillations in the brain is captured using a non-invasive imaging modality.

Embodiment 4

The method according to embodiment 3, wherein the non-invasive imaging modality is functional magnetic resonance imaging.

Embodiment 5

The method according to any of embodiments 1-2, wherein the measuring of hemodynamic low frequency oscillations in the brain is captured using images of electromagnetic radiation reflecting from a surface of the brain.

Embodiment 6

The method according to embodiment 5, wherein the electromagnetic radiation is near or within the range of 300 nm to 800 nm.

Embodiment 7

The method according to any of embodiments 2 and 5-6, further comprising providing two or more image recording devices, and providing a dichroic mirror that separates a wavelength band that is indicative of hemoglobin oxygenation from a wavelength band that is indicative of cerebral blood volume, wherein a first image recording device captures images that are transmitted through the dichroic mirror and a second image recording device captures images that reflected by the dichroic mirror.

Embodiment 8

The method according to embodiment 7, wherein a wavelength band transmitted through the dichroic mirror is in a range of from about 400 nm to about 595 nm and a wavelength band reflected by the dichroic mirror is in a range of from about 640 to 750 nm.

Embodiment 9

The method according to any of embodiments 1-2 and 5-8, further comprising providing two or more bandpass filters.

Embodiment 10

The method according to embodiment 9 wherein a first bandpass filter is about a 500 nm bandpass filter and a second bandpass filter is about a 700 nm bandpass filter.

Embodiment 11

The method according to any of embodiments 2-10, further comprising identifying areas of the brain that exhibit a negative correlation (negatively correlated areas) between the cerebral blood volume low frequency oscillations and the blood oxygenation low frequency oscillations.

Embodiment 12

The method according to embodiment 11, further comprising identifying one or more cause areas, wherein the cause areas are negatively correlated areas that propagate or cause negatively correlated low frequency oscillations in other areas of the brain.

Embodiment 13

The method according to embodiment 12, wherein the one or more cause areas are identified as epileptogenic cortex and are targeted for surgical rescission.

Embodiment 14

The method according to embodiment 12, wherein the one or more cause areas analyzed in combination with one or more other methods of detecting epileptogenic cortices for surgical plan preparation or execution.

Embodiment 15

The method according to any of embodiments 1-14, wherein the method is performed intraoperatively.

Embodiment 16

The method according to any of embodiments 1-15, wherein the method is performed on patients exhibiting focal epilepsy.

Embodiment 17

The method according to any of embodiments 5-6 and 11-16, wherein hardware, software, or a combination of hardware and software is used to separate a wavelength band that is indicative of hemoglobin oxygenation from a wavelength band that is indicative of cerebral blood volume.

Embodiment 18

The method according to any of embodiments 5-17, further comprising co-registering, cropping, and smoothing the images.

Embodiment 19

The method according to any of embodiments 1-18, wherein the low frequency oscillations are in a range of from about 0.01 Hz to about 0.2 Hz

Embodiment 20

The method according to any of embodiments 5-19, further comprising removing artifacts from the images.

Embodiment 21

The method according to any of embodiments 1-20, wherein the method is performed during non-ictal periods.

Embodiment 22

The method according to any of embodiments 1-21, wherein the method further comprises providing external neuronal stimulation.

Embodiment 23

The method according to embodiment 23, wherein the external neuronal stimulation includes peripheral stimulation.

Embodiment 24

The method according to embodiment 23, wherein the external neuronal stimulation includes electrocortical stimulation.

Embodiment 25

The method according to any of embodiments 1-24, wherein the method is used for determining where to place electrodes for ECoG recordings.

Embodiment 30

A method for mapping epileptic cortices, the method comprising:

keeping a patient still and/or stable under normal anesthesia and exposing a brain surface for image capturing;

providing a dichroic mirror with a transmission wavelength range of 400-595 nm and a reflection wavelength range of 640-750 nm;

filtering transmitted wavelengths through a 500 nm bandpass filter and filtering reflected wavelengths through a 700 nm bandpass filter;

providing a first camera to capture the transmitted wavelengths at a transmission port ($Cam_T$) and a second camera to capture the reflected wavelengths at a reflection port ($Cam_R$);

acquiring images of an exposed cortical surface at 500 nm and 700 nm simultaneously, continuously, and intraoperatively using a dynamic intrinsic optical signal imaging (DIOSI) system, wherein both the first camera and the second camera are synchronized, and wherein the first camera and the second camera each acquire a minimum of 300 frames at a minimum rate of two frames per second;

co-registering and cropping the 500 nm images and the 700 nm images to show the same exposed cortex areas, and smoothing the 500 nm images and the 700 nm images using a spatial averaging filter with a 3-by-3 window;

analyzing a time series for each pixel $R(x,y,t)$ in both a time domain and a frequency domain;

filtering the time series $R(p,t)$, where $p=(x,y)$, using a band-pass FIR filter (~0.02-0.1 Hz) to give $R_{low}(p,t)$;

removing artifacts (originating from light source and vessel movements) from $R_{low}(p,t)$ using a principal component analysis method to give $R_{pca}(p,t)$ at each pixel;

generating a power spectral density map using $R_{pca}(p,t)$ for the 500 nm and 700 nm wavelengths;

creating a correlation coefficient map (CCM) by calculating the extent of correlation between $R_{pca}(p,t)$ at 500 nm and 700 nm for each pixel;

extracting pixels with negative correlations from the CCM and removing isolated pixels to leave only spatially connected pixel groups (using an arbitrary threshold of 25 pixels to identify those spatially-connected pixel groups);

classifying the pixels into multiple clusters, using a mean shift clustering method, based upon their temporal profiles in $R_{pca}(p,t)$ at both the 500 nm and 700 nm wavelengths;

denoting $R_{pca}(p,t)$ of each of the clusters as $R_{ci}(p,t)$, wherein subscript i stands for the cluster number; and analyzing the effective and functional connectivity of the clusters as $R_{ci}(p,t)$, wherein the analyzing of the effective and functional connectivity of the clusters includes:

applying Granger causality analysis for non-stationary signals to mean values of $R_{ci}(p,t)$ at 500 nm ($R_{ci}$bar $(p,t)$);

determining influences that originate in A regions and are imposed on B regions (called "directed influences");

labeling A regions Granger-causes and B regions Granger-effects when $R_{ci}$bar $(p,t)$ of A regions are determined to have a directed influence of the $R_{ci}$bar $(p,t)$ of B regions;

using the Granger-causes and Granger-effects as a reference to calculate seed-based correlation coefficients with $R_{pca}(p,t)$ from other pixels within the field of view (FOV) at both the 500 nm and 700 nm wavelengths, to thereby demonstrate functional brain connectivity.

Embodiment 31

The method according to embodiment 30, wherein the one or more Granger-causes are identified as epileptogenic cortex and are targeted for surgical rescission.

Embodiment 32

The method according to embodiment 30, wherein the one or more Granger-causes are analyzed in combination with one or more other methods of detecting epileptogenic cortices for surgical plan preparation or execution.

Embodiment 40

A system for identifying epileptogenic cortices in a brain, the system comprising:

a means for identifying areas in the brain that are exhibiting cerebral blood volume low frequency oscillations;

a means for identifying areas in the brain that are exhibiting blood oxygenation low frequency oscillations;

a means for identifying clusters of the brain that are exhibiting a negative correlation (negatively correlated areas) between the cerebral blood volume low frequency oscillations and the blood oxygenation low frequency oscillations; and a means for identifying one or more cause areas, wherein the cause areas are negatively correlated areas that propagate or cause negatively correlated low frequency oscillations in other areas of the brain.

Embodiment 41

The system according to embodiment 40, wherein the means for identifying areas in the brain that are exhibiting cerebral blood volume low frequency oscillations and the means for identifying areas in the brain that are exhibiting blood oxygenation low frequency oscillations each includes a non-invasive imaging modality.

Embodiment 42

The system according to embodiment 41, wherein the non-invasive imaging modality is functional magnetic resonance imaging.

Embodiment 43

The system for identifying epileptogenic cortices in a brain according to Embodiment 40, wherein the means for identifying areas in the brain that are exhibiting cerebral blood volume low frequency oscillations and the means for identifying areas in the brain that are exhibiting blood oxygenation low frequency oscillations includes:

one or more image recording devices suitable for capturing images of a surface of the brain over time;

one or more processors suitable for separating the images into a wavelength band that is indicative of hemoglobin oxygenation and a wavelength band that is indicative of cerebral blood volume concentration; and one or more processors suitable for identifying low frequency oscillations within the hemoglobin oxygenation indicative wavelength band and suitable for identifying low frequency oscillations within the cerebral blood volume indicative wavelength band.

Embodiment 44

The system according to embodiment 40, wherein the means for identifying areas in the brain that are exhibiting cerebral blood volume low frequency oscillations and the means for identifying areas in the brain that are exhibiting blood oxygenation low frequency oscillations includes:

a dichroic mirror suitable for separating a wavelength band that is indicative of hemoglobin oxygenation and a wavelength band that is indicative of cerebral blood volume concentration;

a first image recording device positioned to capture wavelengths transmitted through the dichroic mirror and a second image recording device positioned to capture wavelengths that are reflected by the dichroic mirror.

Embodiment 45

The system according to embodiment 44, wherein the dichroic mirror has a transmission wavelength range of from about 400 nm to about 595 nm and a reflection wavelength range of from about 640 nm to about 750 nm.

Embodiment 46

The according to any of embodiments 44 or 45, wherein the means for identifying clusters in the brain that are exhibiting cerebral blood volume low frequency oscillations and blood oxygenation low frequency oscillations includes: a first bandpass filter that approximately a 500 nm bandpass filter and a second bandpass filter that is approximately a 700 nm bandpass filter, wherein each of the first bandpass filter and the second bandpass filter is positioned between the dichroic mirror and its respective image recording device.

Embodiment 47

The system according to any of embodiments 44 to 46, wherein the means for identifying areas in the brain that are exhibiting cerebral blood volume low frequency oscillations and the means for identifying areas in the brain that are exhibiting blood oxygenation low frequency oscillations includes: one or one or more processors suitable for identifying hemoglobin oxygenation low frequency oscillations and suitable for identifying cerebral blood volume low frequency oscillations.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Alarcon G, et al. (1997) Origin and propagation of interictal discharges in the acute electrocorticogram. Brain 120: 2259-2282.

Boveroux P, et al. (2010) Breakdown of within-and between-network resting state functional magnetic resonance imaging connectivity during propofol-induced loss of consciousness. Anesthesiology 113(5):1038-1053.

Buxton R B, UludağK, Dubowitz D J, & Liu T T (2004) Modeling the hemodynamic response to brain activation. Neuroimage 23:S220-S233.

Buxton R B (2012) Dynamic models of BOLD contrast. Neuroimage 62(2):953-961.

Cannestra A F, et al. (2000) Temporal and topographical characterization of language cortices using intraoperative optical intrinsic signals. Neuroimage 12(1):41-54.

Cannestra A F, et al. (2001) Temporal spatial differences observed by functional MRI and human intraoperative optical imaging. Cerebral Cortex 11(8):773-782.

Chaplot S, Patnaik L, & Jagannathan N (2006) Classification of magnetic resonance brain images using wavelets as input to support vector machine and neural network. Biomedical Signal Processing and Control 1(1):86-92.

Chen B R, Kozberg M G, Bouchard M B, Shaik M A, & Hillman E M (2014) A critical role for the vascular endothelium in functional neurovascular coupling in the brain. Journal of the American Heart Association 3(3): e000787.

Cheng M A, et al. (1996) Large-dose propofol alone in adult epileptic patients: electrocorticographic results. Anesthesia & Analgesia 83(1):169-174.

Choi H, et al. (2014) Abnormal metabolic connectivity in the pilocarpine-induced epilepsy rat model: a multiscale network analysis based on persistent homology. NeuroImage 99:226-236.

Cui Z & Luan G (2011) A venous malformation accompanying focal cortical dysplasia resulting in a reorganization of language-eloquent areas. Journal of Clinical Neuroscience 18(3):404-406.

Dachet F, et al. (2014) Predicting novel histopathological microlesions in human epileptic brain through transcriptional clustering. Brain:awu350.

Ding Z & White P F (2002) Anesthesia for electroconvulsive therapy. Anesthesia & Analgesia 94(5):1351-1364.

El-Naqa I, Yang Y, Wernick M N, Galatsanos N P, & Nishikawa R M (2002) A support vector machine approach for detection of microcalcifications. Medical Imaging, IEEE Transactions on 21(12):1552-1563.

Fox M D & Raichle M E (2007) Spontaneous fluctuations in brain activity observed with functional magnetic resonance imaging. Nature Reviews Neuroscience 8(9):700-711.

Gasser T, et al. (2005) Intraoperative functional MRI: implementation and preliminary experience. Neuroimage 26(3):685-693.

Glover G H (1999) Deconvolution of Impulse Response in Event-Related BOLD fMRI 1. Neuroimage 9(4):416-429.

Guo L, Rivero D, Dorado J, Rabunal J R, & Pazos A (2010) Automatic epileptic seizure detection in EEGs based on line length feature and artificial neural networks. Journal of neuroscience methods 191(1):101-109.

Haglund M M & Hochman D W (2004) Optical imaging of epileptiform activity in human neocortex. Epilepsia 45(s4):43-47.

Hamilton N B, Attwell D, & Hall C N (2010) Pericyte-mediated regulation of capillary diameter: a component of neurovascular coupling in health and disease. Frontiers in Neuroenergetics 2.

Hufnagel A, Elger C, Nadstawek J, Stoeckel H, & Böker D (1990) Specific response of the epileptic focus to anesthesia with propofol. Journal of Epilepsy 3(1):37-45.

Jayakar P, Duchowny M, & Resnick T J (1994) Subdural monitoring in the evaluation of children for epilepsy surgery. Journal of child neurology 9(2 suppl):2S61-62S66.

Jayakar P, et al. (2008) Epilepsy surgery in patients with normal or nonfocal MRI scans: integrative strategies offer long-term seizure relief. Epilepsia 49(5):758-764.

Jupp B, et al. (2012) Hypometabolism precedes limbic atrophy and spontaneous recurrent seizures in a rat model of TLE. Epilepsia 53(7):1233-1244.

Kalkman C, Traast H, Zuurmond W, & Bovill J (1991) Differential effects of propofol and nitrous oxide on posterior tibial nerve somatosensory cortical evoked potentials during alfentanil anaesthesia. British Journal of Anaesthesia 66(4):483-489.

Krieger S N, Huber L, Poser B A, Turner R, & Egan G F (2014) Simultaneous acquisition of cerebral blood volume-, blood flow-, and blood oxygenation-weighted MRI signals at ultra-high magnetic field. Magnetic Resonance in Medicine.

Krsek P, et al. (2013) Predictors of Seizure©\free outcome after epilepsy surgery for pediatric tuberous sclerosis complex. Epilepsia 54(11):1913-1921.

Lavine M, Haglund M M, & Hochman D W (2011) Dynamic linear model analysis of optical imaging data acquired from the human neocortex. Journal of Neuroscience Methods 199(2):346-362.

Liwnicz B H, Leach J L, Yeh H-S, & Privitera M (1990) Pericyte degeneration and thickening of basement membranes of cerebral microvessels in complex partial seizures: electron microscopic study of surgically removed tissue. Neurosurgery 26(3):409-420.

Lu H, Golay X, Pekar J J, & van Zijl P (2003) Functional magnetic resonance imaging based on changes in vascular space occupancy. Magnetic Resonance in Medicine 50(2):263-274.

Luo Q, et al. (2013) Spatio-temporal Granger causality: a new framework. NeuroImage 79:241-263.

Mallat S G (1989) A theory for multiresolution signal decomposition: the wavelet representation. Pattern Analysis and Machine Intelligence, IEEE Transactions on 11(7):674-693.

Mayhew J E, et al. (1996) Cerebral vasomotion: a 0.1-Hz oscillation in reflected light imaging of neural activity. Neuroimage 4(3):183-193.

McCaslin A F, Chen B R, Radosevich A J, Cauli B, & Hillman E M (2011) In vivo 3D morphology of astrocyte-vasculature interactions in the somatosensory cortex: implications for neurovascular coupling. Journal of Cerebral Blood Flow & Metabolism 31(3):795-806.

Mhuircheartaigh R N, et al. (2010) Cortical and subcortical connectivity changes during decreasing levels of consciousness in humans: a functional magnetic resonance imaging study using propofol. The Journal of Neuroscience 30(27):9095-9102.

Nasiriavanaki M, et al. (2014) High-resolution photoacoustic tomography of resting-state functional connectivity in the mouse brain. Proceedings of the National Academy of Sciences 111(1):21-26.

Ndode-Ekane X, Hayward N, Gröhn O, & Pitkänen A (2010) Vascular changes in epilepsy: functional consequences and association with network plasticity in pilocarpine-induced experimental epilepsy. Neuroscience 166(1):312-332.

Paolicchi J, et al. (2000) Predictors of outcome in pediatric epilepsy surgery. Neurology 54(3):642-642.

Pondal-Sordo M, Diosy D, Téllez-Zenteno J F, Sahjpaul R, & Wiebe S (2007) Usefulness of intracranial EEG in the decision process for epilepsy surgery. Epilepsy research 74(2):176-182.

Ramirez J, et al. (2013) Computer-aided diagnosis of Alzheimer's type dementia combining support vector machines and discriminant set of features. Information Sciences 237: 59-72.

Rayshubskiy A, et al. (2014) Direct, intraoperative observation of ~0.1 Hz hemodynamic oscillations in awake human cortex: implications for fMRI. Neuroimage 87:323-331.

Rigau V, et al. (2007) Angiogenesis is associated with blood-brain barrier permeability in temporal lobe epilepsy. Brain 130(7):1942-1956.

Roebroeck A, Formisano E, & Goebel R (2005) Mapping directed influence over the brain using Granger causality and fMRI. Neuroimage 25(1):230-242.

Sato K, et al. (2002) Intraoperative intrinsic optical imaging of neuronal activity from subdivisions of the human primary somatosensory cortex. Cerebral Cortex 12(3):269-280.

Scanley B E, et al. (1997) Functional magnetic resonance imaging of median nerve stimulation in rats at 2.0 T. Magnetic Resonance in Medicine 37(6):969-972.

Sliwka U, et al. (2001) Spontaneous oscillations in cerebral blood flow velocity give evidence of different autonomic dysfunctions in various types of headache. Headache: The Journal of Head and Face Pain 41(2):157-163.

Sobottka S B, et al. (2013) Intraoperative optical imaging of intrinsic signals: a reliable method for visualizing stimulated functional brain areas during surgery: Clinical article. Journal of Neurosurgery 119(4):853-863.

Sommer B, et al. (2013) Integration of functional neuronavigation and intraoperative MRI in surgery for drug-resistant extratemporal epilepsy close to eloquent brain areas. Neurosurgical Focus 34(4):E4.

Song Y, et al. (2012) Low-frequency pathophysiological characteristics of pediatric epileptic cortex during the interictal period detected using a dual-wavelength imaging system. SPIE Medical Imaging, (International Society for Optics and Photonics), pp 83170V-83170V-83178.

Song Y, Sanganahalli B G, Hyder F, Lin W-C, & Riera J J (2015) Distributions of irritative zones are related to individual alterations of resting-state networks in focal epilepsy. PLos One 10(7): e0134352.

Spreafico R & Blümcke I (2010) Focal cortical dysplasias: clinical implication of neuropathological classification systems. Acta Neuropathologica 120(3):359-367.

Stamatakis E A, Adapa R M, Absalom A R, & Menon D K (2010) Changes in resting neural connectivity during propofol sedation. PLoS One 5(12):e14224.

Subasi A & Gursoy M I (2010) EEG signal classification using PCA, ICA, LDA and support vector machines. Expert Systems with Applications 37(12):8659-8666.

Tharin S & Golby A (2007) Functional brain mapping and its applications to neurosurgery. Neurosurgery 60(4):185-202.

Toronov V, et al. (2000) Near-infrared study of fluctuations in cerebral hemodynamics during rest and motor stimulation: temporal analysis and spatial mapping. Medical Physics 27(4): 801-815.

Wang X, et al. (2012) Effects of propofol and ketamine as combined anesthesia for electroconvulsive therapy in patients with depressive disorder. The Journal of ECT 28(2):128-132.

White B R, Liao S M, Ferradal S L, Inder T E, & Culver J P (2012) Bedside optical imaging of occipital resting-state functional connectivity in neonates. NeuroImage 59(3): 2529-2538.

Winston G P (2013) Epilepsy surgery, vision, and driving: What has surgery taught us and could modern imaging reduce the risk of visual deficits? Epilepsia 54(11):1877-1888.

Yalcin S, et al. (2012) Ketofol in electroconvulsive therapy anesthesia: two stones for one bird. Journal of Anesthesia 26(4):562-567.

Yang Y, Gu H, & Stein E A (2004) Simultaneous MRI acquisition of blood volume, blood flow, and blood oxygenation information during brain activation. Magnetic Resonance in Medicine 52(6):1407-1417.

Zavar M, Rahati S, Akbarzadeh-T M-R, & Ghasemifard H (2011) Evolutionary model selection in a wavelet-based support vector machine for automated seizure detection. Expert Systems with Applications 38(9):10751-10758.

Zijlmans M, et al. (2012) Epileptic high-frequency oscillations in intraoperative electrocorticography: The effect of propofol. Epilepsia 53(10):1799-1809.

What is claimed is:

1. A method for identifying epileptogenic cortices in a brain, surgical planning, and epileptogenic resection, the method comprising:
    detecting areas in the brain that are undergoing cerebral blood volume low frequency oscillations;
    detecting areas in the brain that are undergoing blood oxygenation low frequency oscillations;
    mapping clusters of the brain in which the cerebral blood volume low frequency oscillations are negatively correlated with the blood oxygenation low frequency oscillations; and
    analyzing a time based relationship between the clusters of the brain that are undergoing negatively correlated low frequency oscillations to determine cause areas, which are areas of the brain that are causing negatively correlated low frequency oscillations to occur elsewhere,
    the detecting of areas in the brain that are undergoing cerebral blood volume low frequency oscillations and the detecting of areas in the brain that are undergoing blood oxygenation low frequency oscillations being accomplished using a non-invasive imaging modality, and
    the method further comprising using hardware, software, or a combination of hardware and software to separate a wavelength band that is indicative of hemoglobin oxygenation from a wavelength band that is indicative of cerebral blood volume.

2. The method according to claim 1, further comprising: identifying the cause areas as potential epileptogenic cortex and using the identified cause areas for surgical planning or guiding epileptogenic resection intraoperatively.

3. The method according to claim 2, the detecting of areas in the brain that are undergoing cerebral blood volume low frequency oscillations and the detecting of areas in the brain that are undergoing blood oxygenation low frequency oscillations being accomplished by capturing images of a surface of the brain within a wavelength range of from about 300 nm to about 800 nm.

4. The method according to claim 3, the detecting of areas in the brain that are undergoing cerebral blood volume low frequency oscillations being accomplished by analyzing images within a wavelength range of from about 400 nm to about 595 nm, and the detecting of areas in the brain that are undergoing blood oxygenation low frequency oscillations being accomplished by analyzing images having a wavelength range of from about 640 to about 750 nm.

5. The method according to claim 2, the detecting of areas in the brain that are undergoing cerebral blood volume low frequency oscillations and the detecting of areas in the brain that are undergoing blood oxygenation low frequency oscillations being accomplished by capturing images of a surface of the brain with a wavelength band that is indicative of cerebral blood volume and capturing images of the surface of the brain with a wavelength band that is indicative of blood oxygenation, respectively.

6. The method according to claim 5, the capturing images of the surface of the brain with the wavelength band that is indicative of cerebral blood volume and the capturing images of the surface of the brain with the wavelength band that is indicative of blood oxygenation both including using a dichroic mirror.

7. The method according to claim 6, the capturing images of the surface of the brain with the wavelength band that is indicative of cerebral blood volume and the capturing images of the surface of the brain with the wavelength band that is indicative of blood oxygenation being accomplished using bandpass filters in addition to the dichroic mirror.

8. The method according to claim 2, the method being performed on a patient having focal epilepsy.

9. The method according to claim 1, the non-invasive imaging modality being functional magnetic resonance imaging.

10. The method according to claim 5, further comprising co-registering, cropping, and smoothing the images.

11. The method according to claim 2, the low frequency oscillations being in a range of from about 0.02 Hz to about 0.1 Hz.

12. The method according to claim 1, further comprising providing external neuronal stimulation.

13. The method according to claim 12, the external neuronal stimulation comprising at least one of peripheral stimulation and electrocortical stimulation.

14. The method according to claim 1, further comprising determining where to place electrodes for ECoG recordings, based on the time based relationship between the clusters of the brain that are undergoing negatively correlated low frequency oscillations.

15. A method for identifying epileptogenic cortices in a brain, surgical planning, and epileptogenic resection, the method comprising:
    detecting areas in the brain that are undergoing cerebral blood volume low frequency oscillations;
    detecting areas in the brain that are undergoing blood oxygenation low frequency oscillations;
    mapping clusters of the brain in which the cerebral blood volume low frequency oscillations are negatively correlated with the blood oxygenation low frequency oscillations;
    analyzing a time based relationship between the clusters of the brain that are undergoing negatively correlated low frequency oscillations to determine cause areas, which are areas of the brain that are causing negatively correlated low frequency oscillations to occur elsewhere; and identifying the cause areas as potential epileptogenic cortex and using the identified cause areas for surgical planning or guiding epileptogenic resection intraoperatively, the detecting of areas in the brain that are undergoing cerebral blood volume low frequency oscillations and the detecting of areas in the brain that are undergoing blood oxygenation low frequency oscillations being accomplished by capturing images of a surface of the brain with a wavelength band that is indicative of cerebral blood volume and capturing images of the surface of the brain with a wavelength band that is indicative of blood oxygenation, respectively, the capturing images of the surface of the brain with the wavelength band that is indicative of cerebral blood volume and the capturing images of the surface of the brain with the wavelength band that is indicative of blood oxygenation both comprising using a dichroic mirror, the capturing images of the surface of the brain with the wavelength band that is indicative of cerebral blood volume and the capturing images of the surface of the brain with the wavelength band that is indicative of blood oxygenation being accomplished using bandpass filters in addition to the dichroic mirror, the method being performed on a patient having focal epilepsy, and the method further comprising co-registering, cropping, and smoothing the images.

16. The method according to claim 15, the wavelength band that is indicative of cerebral blood volume being from 400 nm to 595 nm, and the wavelength band that is indicative of blood oxygenation being from 640 nm to 750 nm, and the low frequency oscillations being in a range of from 0.02 Hz to 0.1 Hz.

17. The method according to claim 15, further comprising determining where to place electrodes for electrocorticography recordings, based on the time based relationship between the clusters of the brain that are undergoing negatively correlated low frequency oscillations.

18. A method for identifying epileptogenic cortices in a brain, surgical planning, and epileptogenic resection, the method comprising:

detecting areas in the brain that are undergoing cerebral blood volume low frequency oscillations;

detecting areas in the brain that are undergoing blood oxygenation low frequency oscillations;

mapping clusters of the brain in which the cerebral blood volume low frequency oscillations are negatively correlated with the blood oxygenation low frequency oscillations;

analyzing a time based relationship between the clusters of the brain that are undergoing negatively correlated low frequency oscillations to determine cause areas, which are areas of the brain that are causing negatively correlated low frequency oscillations to occur elsewhere; and identifying the cause areas as potential epileptogenic cortex and using the identified cause areas for surgical planning or guiding epileptogenic resection intraoperatively, the detecting of areas in the brain that are undergoing cerebral blood volume low frequency oscillations being accomplished by capturing images using functional magnetic resonance imaging and analyzing the images within a wavelength range of from 400 nm to 595 nm, and the detecting of areas in the brain that are undergoing blood oxygenation low frequency oscillations being accomplished by capturing images using functional magnetic resonance imaging and analyzing images having a wavelength range of from 640 to 750 nm, the method being performed on a patient having focal epilepsy, the detecting of areas in the brain that are undergoing cerebral blood volume low frequency oscillations and the detecting of areas in the brain that are undergoing blood oxygenation low frequency oscillations being accomplished using a non-invasive imaging modality, the method further comprising using hardware, software, or a combination of hardware and software to separate a wavelength band that is indicative of hemoglobin oxygenation from a wavelength band that is indicative of cerebral blood volume, the low frequency oscillations being in a range of from 0.02 Hz to 0.1 Hz, and the method further comprising determining where to place electrodes for electrocorticography recordings, based on the time based relationship between the clusters of the brain that are undergoing negatively correlated low frequency oscillations.

* * * * *